US009125657B2

(12) United States Patent
Ray et al.

(10) Patent No.: US 9,125,657 B2
(45) Date of Patent: *Sep. 8, 2015

(54) METHODS AND APPARATUS FOR STORAGE AND/OR INTRODUCTION OF IMPLANT FOR HOLLOW ANATOMICAL STRUCTURE

(75) Inventors: Miranda M. Ray, San Jose, CA (US); Hoa D. Nguyen, San Jose, CA (US); John W. Rodriguez, San Jose, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/390,574

(22) PCT Filed: Jun. 21, 2011

(86) PCT No.: PCT/US2011/041143
§ 371 (c)(1),
(2), (4) Date: Feb. 15, 2012

(87) PCT Pub. No.: WO2011/163157
PCT Pub. Date: Dec. 29, 2011

(65) Prior Publication Data
US 2012/0277756 A1    Nov. 1, 2012

Related U.S. Application Data

(60) Provisional application No. 61/357,095, filed on Jun. 22, 2010, provisional application No. 61/357,952, filed on Jun. 23, 2010.

(51) Int. Cl.
*A61M 29/00* (2006.01)
*A61B 17/12* (2006.01)
(Continued)

(52) U.S. Cl.
CPC ..... *A61B 17/12022* (2013.01); *A61B 17/12109* (2013.01); *A61B 17/12181* (2013.01);
(Continued)

(58) Field of Classification Search
CPC .. A61B 17/12022–17/12045; A61B 17/12109; A61B 17/12131; A61B 17/12159–17/12177; A61B 2017/1205–2017/12095
USPC ............. 606/1, 108, 139, 144, 191–200, 213; 623/1.11–1.12, 1.23, 23.72–23.76
See application file for complete search history.

(56) References Cited

U.S. PATENT DOCUMENTS 4,988,356 A * 1/1991 Crittenden et al. ........... 606/192
5,171,222 A * 12/1992 Euteneuer et al. ......... 604/103.1
(Continued)

FOREIGN PATENT DOCUMENTS

DE    20009815    8/2000
WO    WO 99/11180    3/1999

OTHER PUBLICATIONS

International Search Report on related PCT application (PCT/US2011/041143) from International Searching Authority (EPO) dated Jan. 4, 2012.

(Continued)

*Primary Examiner* — Katherine Rodjom
*Assistant Examiner* — Jonathan Hollm
(74) *Attorney, Agent, or Firm* — Thomas M. Johnston, Esq.

(57) ABSTRACT

One embodiment of the apparatus comprises a housing with a sheath portion projecting distally therefrom. The sheath portion has a sheath with a lumen, and a bearing surface in the sheath lumen or aligned with the sheath lumen, and located at or near a distal end of the sheath. The implant is at least partially positioned in the apparatus, and comprises an implant body and a tether connected to the implant body. The tether extends from the implant body distally within the sheath portion and around the bearing surface, where the tether changes direction, and extends back proximally from the bearing surface along and within the sheath portion. The apparatus is configured to move the first tether portion proximally and thereby draw the implant body distally along and within the sheath lumen.

15 Claims, 23 Drawing Sheets

(51) Int. Cl.
  *A61B 17/04* (2006.01)
  *A61B 17/00* (2006.01)
  *A61B 17/32* (2006.01)
  *A61B 19/00* (2006.01)

(52) U.S. Cl.
  CPC ......... *A61B17/0467* (2013.01); *A61B 17/0482* (2013.01); *A61B 2017/0046* (2013.01); *A61B 2017/00336* (2013.01); *A61B 2017/00398* (2013.01); *A61B 2017/00513* (2013.01); *A61B 2017/0496* (2013.01); *A61B 2017/12054* (2013.01); *A61B 2017/320052* (2013.01); *A61B 2019/307* (2013.01)

(56) References Cited

U.S. PATENT DOCUMENTS

| | | | | |
|---|---|---|---|---|
| 5,334,187 | A | * | 8/1994 | Fischell et al. ............ 604/102.02 |
| 6,077,276 | A | | 6/2000 | Kontos |
| 7,946,453 | B2 | * | 5/2011 | Voegele et al. ............... 222/134 |
| 2002/0123755 | A1 | * | 9/2002 | Lowe et al. ................... 606/108 |
| 2003/0023262 | A1 | | 1/2003 | Welch |
| 2004/0181239 | A1 | * | 9/2004 | Dorn et al. .................... 606/108 |
| 2004/0260380 | A1 | * | 12/2004 | Marco et al. ................. 623/1.11 |
| 2005/0085851 | A1 | | 4/2005 | Fiehler et al. |
| 2005/0107827 | A1 | | 5/2005 | Paprocki |
| 2005/0283182 | A1 | * | 12/2005 | Pierce et al. .................. 606/200 |
| 2006/0212127 | A1 | | 9/2006 | Karabey et al. |
| 2006/0229668 | A1 | | 10/2006 | Prestezog et al. |
| 2007/0038245 | A1 | | 2/2007 | Morris et al. |
| 2007/0203508 | A1 | | 8/2007 | White et al. |
| 2008/0112751 | A1 | | 5/2008 | Sheets et al. |
| 2009/0254169 | A1 | | 10/2009 | Spenser et al. |
| 2011/0034987 | A1 | * | 2/2011 | Kennedy ...................... 623/1.11 |

OTHER PUBLICATIONS

Written Opinion on related PCT application (PCT/US2011/041143) from International Searching Authority (EPO) dated Jan. 4, 2012.
U.S. Appl. No. 13/165,170, filed Jun. 21, 2011, Miranda M. Ray, 2011/0313506, Notice of Allowance May 11, 2013.
U.S. Appl. No. 13/165,245, filed Jun. 21, 2011, Ray et al., 2011/0313507, Office Action Mar. 1, 2013.
International Preliminary Report on Patentability on related PCT application (PCT/US2011/041143) from the International Bureau of WIPO dated Jan. 10, 2013.

* cited by examiner

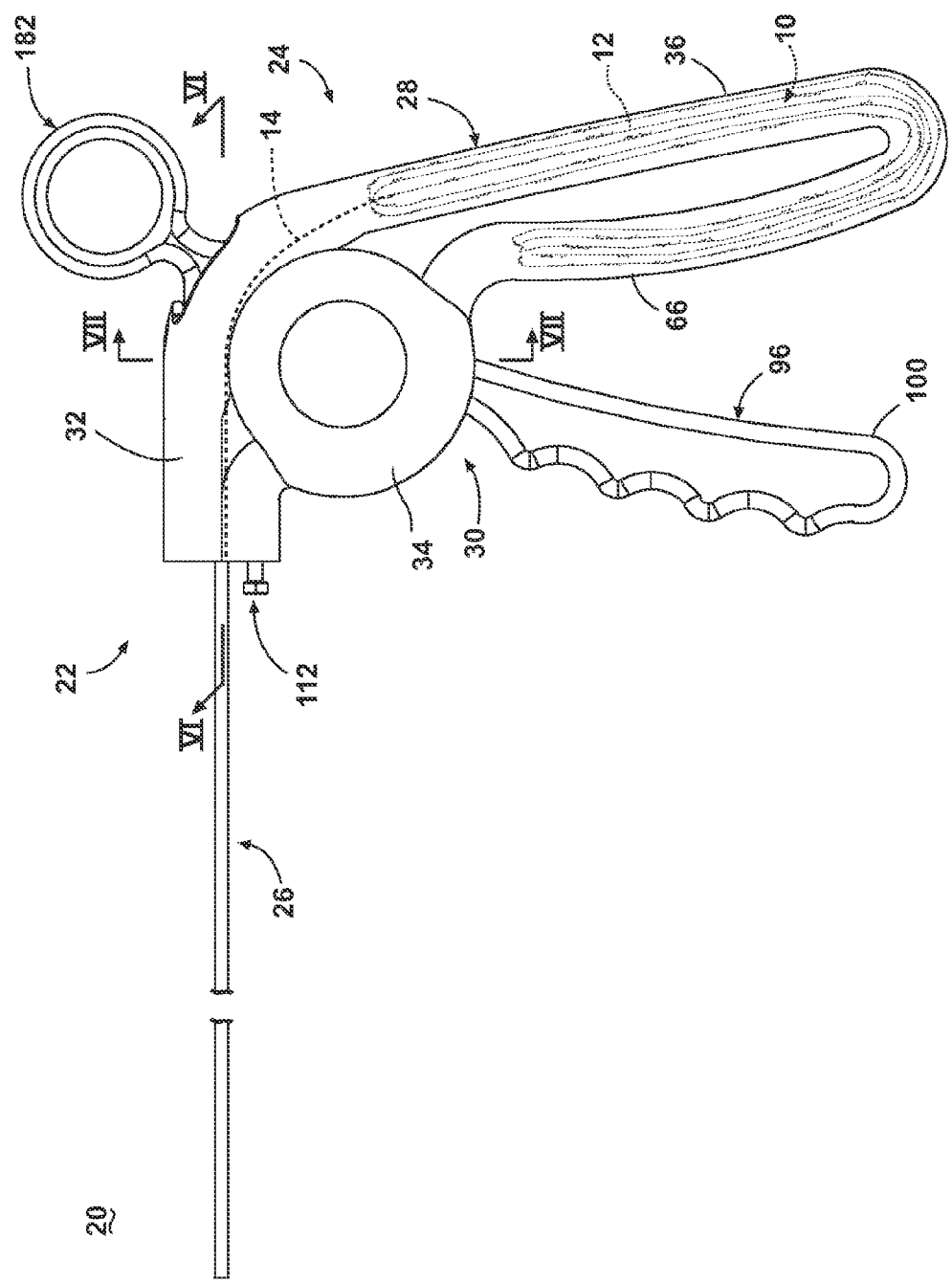

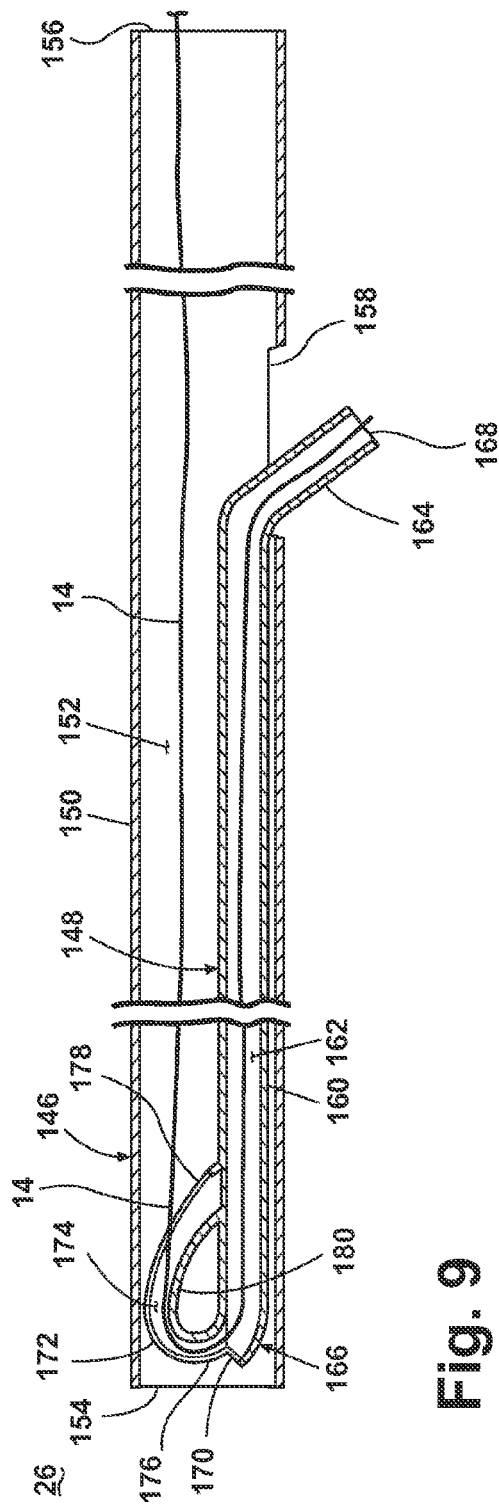
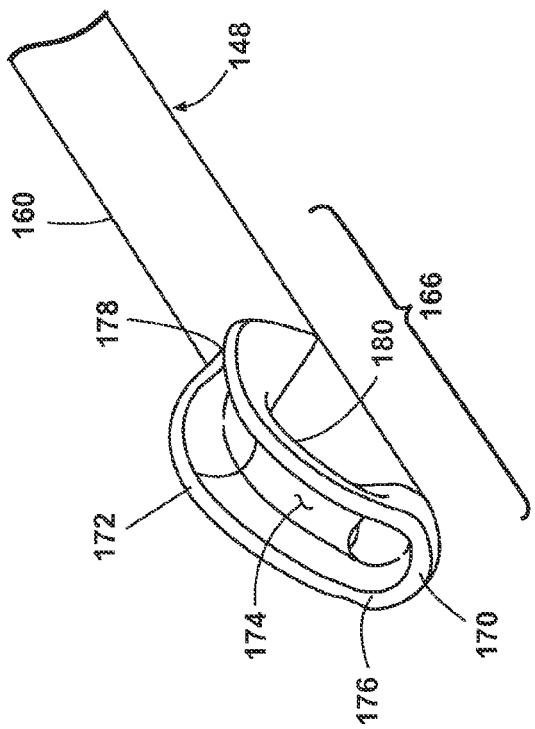
Fig. 9
Fig. 10

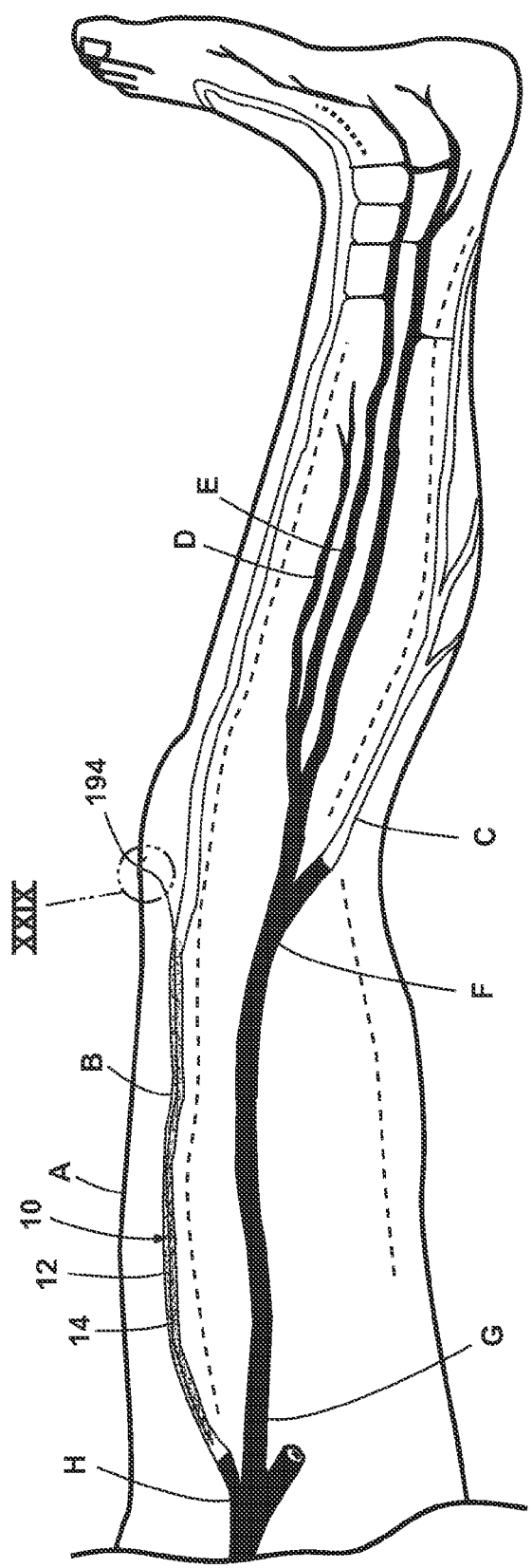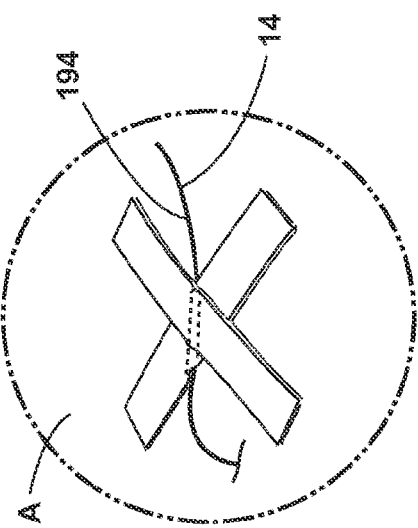
Fig. 28
Fig. 29

METHODS AND APPARATUS FOR STORAGE AND/OR INTRODUCTION OF IMPLANT FOR HOLLOW ANATOMICAL STRUCTURE

CROSS-REFERENCE TO RELATED APPLICATIONS

This application is a national phase filing, under 35 U.S.C. §371(c), of the International Application No. PCT/US2011/041143, filed Jun. 21, 2011, which claims priority to provisional application Ser. No. 61/357,095, filed on Jun. 22, 2010, and provisional application Ser. No. 61/357,952, filed on Jun. 23, 2010. The entire contents of each of the priority-applications are hereby incorporated by reference.

TECHNICAL FIELD

The present invention relates to occluding hollow anatomical structures.

BACKGROUND

Referring to FIG. 1, the human venous system of the leg A comprises the superficial venous system, shown in white, and the deep venous system, shown in black, with perforating veins connecting the two systems. The superficial system includes the long or great saphenous vein B and the small saphenous vein C. The deep venous system includes the anterior and posterior tibial veins D, E, which unite to form the popliteal vein F, which in turn becomes the femoral vein G when joined by the short saphenous vein C. The femoral vein G and the great saphenous vein B join at the sapheno-femoral junction H.

The venous system contains numerous one-way valves for directing antegrade blood flow back to the heart. When an incompetent valve is in the flow path, the valve is unable to close, and retrograde flow of the blood away from the heart cannot be stopped. When a venous valve fails, increased strain and pressure occur within the lower venous sections and overlying tissues, sometimes leading to additional, distal valvular failure. Two venous conditions or symptoms that often result from valve failure are varicose veins and more symptomatic chronic venous insufficiency. Current treatments of venous insufficiency include surgical procedures such as vein stripping, vein-segment transplant, and ligation by ablation.

Vein stripping typically consists of tying off, or ligating, and removing the saphenous vein. Vein segment transplant has been employed in certain organ transplant procedures; however, it is not generally employed in the superficial venous system in humans. Ligation by ablation involves the cauterization or coagulation of vascular lumina using thermal energy applied through a delivery device. Energy introduced into the vein lumen causes the vein wall to shrink in cross-sectional diameter or completely collapse, thereby reducing or completely blocking blood flow through the vein.

An alternative treatment involves placement of an occluding implant in the hollow anatomical structure, such as the great saphenous vein. As an example, the implant can be a fibrous body, optionally textured to impart bulk. The implant causes a partial occlusion of the hollow anatomical structure, followed by a complete or substantially complete occlusion, such as by formation of an organic fibrotic occlusion resulting from the body's natural foreign body healing response.

SUMMARY

The various embodiments of the present methods and apparatus have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One embodiment comprises an apparatus for delivering an implant. The apparatus comprises a housing, a sheath portion projecting distally away from the housing, the sheath portion having a sheath with a sheath lumen, and a bearing surface in the sheath lumen or aligned with the sheath lumen, and located at or near a distal end of the sheath. The implant is at least partially positioned in the apparatus, and comprises an implant body and a tether connected to the implant body. The tether has a first portion that extends from the implant body distally within the sheath portion and around the bearing surface, where the tether changes direction, and extends back proximally, as a second portion, from the bearing surface along and within the sheath portion. The apparatus is configured to move the first tether portion proximally and thereby draw the implant body distally along and within the sheath lumen.

Further optional features and variations of this embodiment are presented in the following paragraphs. The present disclosure contemplates and includes employing these optional features and variations in the third embodiment (or in any other embodiment summarized or described herein), either alone or in any feasible combination of two or more such optional features and variations.

The implant body can optionally be bioabsorbable and comprise a collection of bioabsorbable fibers. As still further options, the tether can be bioabsorbable and inelastic. As still further options, the implant body can be radially self-expanding.

The apparatus can optionally further comprise a reel that is coupled to the tether and configured to move the first tether portion proximally, and thereby draw the implant body distally along and within the sheath lumen.

The sheath portion can optionally further comprise an inner member that extends distally along and within the sheath lumen, and the bearing surface is positioned at or near a distal end of the inner member. As still further options, the inner member can comprise an inner member lumen extending within the inner member, and the first tether portion can extend along and within the inner member lumen. As still further options, the sheath can be retractable proximally to expose the inner member. As still further options, the apparatus can further comprise a sheath parting member that projects into the sheath lumen through an opening in a sidewall of the sheath, wherein the sheath parting member is configured to part the sidewall of the sheath as the sheath is retracted proximally. As still further options, the sheath parting member can comprise a sharpened blade that cuts through the sheath sidewall as the sheath is retracted. As still further options, the sheath sidewall can have a score line and the sheath parting member can comprise a post or unsharpened wedge that splits the sheath sidewall along the score line as the sheath is retracted. As still further options, the inner member can comprise an inner member lumen extending within the inner member, and the first tether portion can extend along and within the inner member lumen; and a proximal portion of the inner member can comprise a lateral projection that turns and extends radially outward to pass out of the sheath lumen, at a location proximal of the sheath parting member, such that the lateral projection of the inner member can be positioned between two parted portions of the sheath sidewall as the sheath is retracted proximally and the sheath sidewall is parted. As still further options, the tether can passes through the lateral projection of the inner member such that the inner member prevents contact between the sheath sidewall and the tether as the sheath is retracted proximally and the sheath sidewall is parted.

Another embodiment comprises an apparatus for delivering an implant. The apparatus comprises a housing; and a sheath portion extending distally away from the housing, the sheath portion having a sheath with a sheath lumen. The implant comprises an implant body and a tether connected to the implant body, and the implant has a first position in which the implant body is at least partially located within the housing, and the tether extends distally along and within the sheath portion, and turns to extend back proximally along and within the sheath portion. The apparatus further comprises a reel that is configured to wind the tether and thereby draw the implant body distally along and within the sheath lumen to a second position.

Further optional features and variations of this embodiment are presented in the following paragraphs. The present disclosure contemplates and includes employing these optional features and variations in the fourth embodiment (or in any other embodiment summarized or described herein), either alone or in any feasible combination of two or more such optional features and variations.

The sheath portion can optionally be sized and configured for percutaneous insertion into a blood vessel.

The implant body can optionally be self-expanding, and the implant body can be in an expanded configuration when the implant is in the first position. As still further options, the implant body can be stored in the housing when the implant is in the first position, and no portion of the implant body can be in the sheath lumen. As still further options, the implant body can be bioabsorbable and comprise a bundle of fibers. As still further options, the implant body can be in a compressed configuration when the implant is in the second position.

The sheath portion can optionally further comprise an inner member extending along and within the sheath lumen, the inner member providing a bearing surface at or near the distal end of the sheath, within or aligned with the sheath lumen. As still further options, the tether can have a first portion that extends from the implant body distally within the sheath portion and around the bearing surface, where the tether can change direction, and extend back proximally, as a second portion, from the bearing surface along and within the sheath portion. As still further options, the inner member can comprise an inner member lumen extending within the inner member, and the first tether portion can extend along and within the inner member lumen, proximally toward the reel. As still further options, the sheath can be retractable proximally to expose the inner member. As still further options, the apparatus can further comprise a sheath parting member that projects into the sheath lumen through an opening in a sidewall of the sheath, wherein the sheath parting member is configured to part the sidewall of the sheath as the sheath is retracted proximally. As still further options, the sheath parting member can comprise\ a sharpened blade that cuts through the sheath sidewall as the sheath is retracted. As still further options, the sheath sidewall can have a score line and the sheath parting member can comprise a post or unsharpened wedge that splits the sheath sidewall along the score line as the sheath is retracted. As still further options, the inner member can comprise an inner member lumen extending within the inner member, and the first tether portion can extends along and within the inner member lumen; and a proximal portion of the inner member can comprise a lateral projection that turns and extends radially outward to pass out of the sheath lumen, at a location proximal of the sheath parting member, such that the lateral projection of the inner member is positioned between two parted portions of the sheath sidewall as the sheath is retracted proximally and the sheath sidewall is parted.

Another embodiment comprises apparatus for delivering an implant. The apparatus comprises a housing, an outer sheath projecting distally away from the housing, the outer sheath having an outer sheath lumen, and an inner sheath projecting distally away from the housing at least partially within the outer sheath lumen, the inner sheath having an inner sheath lumen. The implant is at least partially positioned in the apparatus, and comprises an implant body and a tether connected to the implant body. The apparatus is configured to advance the implant body distally within the inner sheath lumen without relative movement of the outer sheath and the inner sheath.

Another embodiment comprises a method of preparing a vascular implant for subsequent deployment into a blood vessel, the implant having an implant body and a tether connected to the implant body. The method comprises moving the implant body from a first position, distally along and within a lumen of a sheath that is sized and configured for percutaneous insertion into a blood vessel, to a second position in a distal portion of the sheath lumen. Moving the implant body to the second position comprises drawing a portion of the tether proximally by applying force to the tether at a location outside of the sheath and proximal of the second position.

Further optional features and variations of this embodiment are presented in the following paragraphs. The present disclosure contemplates and includes employing these optional features and variations in the fifth embodiment (or in any other embodiment summarized or described herein), either alone or in any feasible combination of two or more such optional features and variations.

Applying force to the tether can optionally comprise winding the tether onto a reel. As still further options, the method can further comprise changing a direction of force applied by the tether with a bearing surface around which the tether turns, the bearing surface being located at or near a distal end of the sheath. As still further options, moving the implant body to the second position can comprise compressing the implant body while advancing it from the first position into a proximal portion of the sheath lumen. As still further options, the implant body can be self-expanding, and the implant body can be in an expanded condition when in the first position. As still further options, the first position can comprise a storage position within a delivery apparatus. As still further options, the method can further comprise inserting the sheath into a blood vessel and moving the implant body to the second position while the sheath is inside the blood vessel.

Another embodiment comprises a method of delivering into a hollow anatomical structure (HAS) a bioabsorbable implant having an implant body and a tether connected to the implant body. The method is performed with the assistance of a delivery apparatus having a sheath assembly with an outer sheath and an inner member extending along an inner lumen of the outer sheath to a distal end portion of the inner member, which inner member distal end portion forms a bearing surface near a distal end of the outer sheath. The tether includes a distally-extending portion that extends distally from the implant body along and within the outer sheath lumen, and turns around the bearing surface to form a proximally-extending portion that extends proximally from the bearing surface along and within the sheath assembly. The method comprises inserting the sheath assembly into the HAS, wherein inserting the sheath assembly comprises inserting the outer sheath and inner member simultaneously; moving the implant body distally along and within the outer sheath lumen by moving the proximally-extending portion of the implant tether proximally, so that a distal portion of the implant body advances to a distal portion of the outer sheath; and withdrawing the outer sheath from the inner member and the implant body, while holding the implant body in its distally-advanced position with the inner member and the tether.

Further optional features and variations of this embodiment are presented in the following paragraphs. The present disclosure contemplates and includes employing these optional features and variations in the first embodiment (or in any other embodiment summarized or described herein), either alone or in any feasible combination of two or more such optional features and variations.

Inserting the sheath assembly into the HAS can optionally comprise inserting the sheath assembly through a tissue tract extending from the skin surface to the HAS, and the method can optionally further comprise severing the tether and withdrawing the inner member from the HAS, and leaving the implant in a state wherein the implant body resides within the HAS and the tether extends from a distal end of the implant body and into the tissue tract, thereby facilitating anchoring of the implant body with the tether.

Inserting the sheath assembly into the HAS can optionally comprise inserting the sheath assembly through a tissue tract extending from the skin surface to HAS, and the method can optionally further comprise severing the tether and withdrawing the inner member from the HAS, and leaving the implant in a state wherein the implant body resides within the HAS, and the tether and the implant body extend from the HAS into the tissue tract, thereby facilitating anchoring of the implant body with the tether.

The method can optionally further comprise severing the tether and withdrawing the inner member from the HAS, leaving the implant body and tether in the HAS, and allowing the implant body to engage an inner wall of the HAS. As still further options, the inner member can comprise an inner sheath having an internal lumen, and the proximally-extending portion of the tether can extend along and within the inner sheath lumen; and withdrawing the inner member from the HAS can comprise allowing the tether to slide out of the inner sheath lumen as the inner member is withdrawn. As still further options, the HAS can be a blood vessel, and the method can further comprise occluding the blood vessel with the implant.

The outer sheath can optionally have a sidewall, and the method can further comprise parting the sidewall of the outer sheath while withdrawing the outer sheath. As still further options, parting the sidewall of the outer sheath can comprise forming a longitudinal opening in the sidewall, thereby allowing the tether to pass through the sidewall opening as the outer sheath is withdrawn.

The method can further optionally comprise holding the delivery apparatus in a first hand of a user while actuating the delivery apparatus with the first hand to cause the implant body to move distally along and within the outer sheath lumen. As still further options, actuating the delivery apparatus with the first hand can comprise causing the implant body to move to a distal-most position within the outer sheath where a distal end of the implant body is near a distal end of the outer sheath. As still further options, the method can comprise holding and operating an ultrasound probe with a second hand of the user while holding the delivery apparatus with the first hand. As still further options, the method can comprise actuating the delivery apparatus with the first hand while holding and operating the ultrasound probe with the second hand.

Moving the proximally-extending portion of the tether proximally can optionally comprise winding the tether onto a reel.

Another embodiment comprises a method of delivering into a hollow anatomical structure (HAS) an implant having an implant body and a tether connected to the implant body. The method is performed with the assistance of a delivery apparatus having a sheath portion with a sheath and a bearing surface near a distal end of the sheath, wherein the sheath has an inner lumen and the tether includes a distally-extending portion that extends distally from the implant body along and within the sheath portion, and turns around the bearing surface to form a proximally-extending portion that extends proximally from the bearing surface along and within the sheath portion. The method comprises inserting the sheath portion into the HAS; moving the implant body distally along and within the sheath lumen by moving the proximally-extending portion of the implant tether proximally, so that a distal portion of the implant body advances to a distal portion of the sheath; and withdrawing the sheath from the implant body, while holding the implant body in its distally-advanced position with the tether.

Further optional features and variations of this embodiment are presented in the following paragraphs. The present disclosure contemplates and includes employing these optional features and variations in the second embodiment (or in any other embodiment summarized or described herein), either alone or in any feasible combination of two or more such optional features and variations.

The sheath portion can optionally comprise an outer sheath and an inner member which extends distally within the outer sheath to a distal portion of the outer sheath; the inner member can form the bearing surface near a distal end of the inner member; and holding the implant body in its distally-advanced position can comprise holding the implant with the tether and the inner member. As still further options, the inner member can comprise an inner sheath having an internal lumen, and the proximally-extending portion of the tether can extend along and within the inner sheath lumen; and the method can further comprise withdrawing the inner member from the HAS while allowing the tether to slide out of the inner sheath lumen as the inner member is withdrawn.

Inserting the sheath portion into the HAS can optionally comprise inserting the sheath portion through a tissue tract extending from the skin surface to the HAS; and the method can further comprise severing the tether and leaving the implant in a state wherein the implant body resides within the HAS and the tether extends from a distal end of the implant body and into the tissue tract, thereby facilitating anchoring of the implant body with the tether.

Inserting the sheath portion into the HAS can optionally comprise inserting the sheath portion through a tissue tract extending from the skin surface to the HAS; and the method can further comprise severing the tether and leaving the implant in a state wherein the implant body resides within the HAS and the tether and the implant body extend from the HAS and into the tissue tract, thereby facilitating anchoring of the implant body with the tether.

The method can further optionally comprise severing the tether, leaving the implant body and tether in the HAS, and allowing the implant body to engage an inner wall of the HAS.

The HAS can optionally be a blood vessel; and the method can further comprise occluding the blood vessel with the implant.

The sheath can optionally have a sidewall; and the method can further comprise parting the sidewall of the sheath while withdrawing the sheath. As still further options, Parting the sidewall of the sheath can comprise forming a longitudinal opening in the sidewall, thereby allowing the tether to pass through the sidewall opening as the outer sheath is withdrawn.

The method can further optionally comprise holding the delivery apparatus in a first hand of a user while actuating the delivery apparatus with the first hand to cause the implant body to move distally along and within the sheath lumen. As still further options, actuating the delivery apparatus with the first hand can comprise causing the implant body to move to a distal-most position within the sheath where a distal end of the implant body is near a distal end of the outer sheath. As still further options, the method can further comprise holding and operating an ultrasound probe with a second hand of the user while holding the delivery apparatus with the first hand. As still further options, the method can further comprise actuating the delivery apparatus with the first hand while holding and operating the ultrasound probe with the second hand.

Moving the proximally-extending portion of the tether proximally can optionally comprise winding the tether onto a reel.

Inserting the sheath portion into the HAS can optionally be performed before advancing the implant body to the distal portion of the sheath.

BRIEF DESCRIPTION OF THE DRAWINGS

FIG. 3 is an elevation view of a system according to one embodiment comprising the implant of FIG. 2 and an embodiment of an apparatus for storage and/or introduction of the implant into a hollow anatomical structure;

FIG. 9 is an enlarged sectional view of the sheath assembly, particularly the distal and proximal ends of the sheath assembly, of the apparatus of FIG. 3 and the tether of the implant of FIG. 2;

FIG. 10 is a perspective view of the distal end of an inner sheath of the sheath assembly from FIG. 9; the tether is not shown for clarity;

FIGS. 16-29 illustrate various exemplary stages of a method of use of the system according to one embodiment:

FIG. 16 illustrates the leg of FIG. 1 with the sheath assembly of FIG. 3 located in the greater saphenous vein of the leg;

FIG. 17 is an enlarged view of the region labeled "XVII" in FIG. 16;

FIG. 18 is a view similar to FIG. 16, illustrating the actuation of an introducer assembly of the apparatus of FIG. 3;

FIG. 19 is a view similar to FIG. 17 illustrating the forces on the tether of the implant of FIG. 2 during actuation of the introducer assembly;

FIG. 20 is a view similar to FIG. 11 during advancement of the implant of FIG. 2 through the sheath assembly of FIG. 3;

FIG. 21 is a view similar to FIG. 20 during further advancement of the implant of FIG. 2 through the sheath assembly of FIG. 3;

FIG. 22 is a view similar to FIG. 18 after removal of an outer sheath of the sheath assembly from the apparatus;

FIG. 23 is a schematic underside view of the sheath cutting assembly from FIG. 8 to illustrate the cutting of the outer sheath during removal of the outer sheath of the sheath assembly from the apparatus;

FIG. 24 is a view similar to FIG. 19 during retraction of the outer sheath of the sheath assembly from the greater saphenous vein;

FIG. 25 is a view similar to FIG. 24 after removal of the outer sheath of the sheath assembly from the greater saphenous vein;

FIG. 26 is a view similar to FIG. 8, but with the sheath shown, during cutting of the tether of the implant of FIG. 2;

FIG. 27 is a view similar to FIG. 25 illustrating the implant in the greater saphenous vein after removal of the inner sheath from the greater saphenous vein;

FIG. 28 illustrates the leg after implantation of the implant in the greater saphenous vein; and FIG. 29 is a plan view of the exterior region of the leg labeled "XXIX" in FIG. 28.

DETAILED DESCRIPTION

The disclosed embodiments relate generally to a method and apparatus for storage and/or introduction of an implant into a hollow anatomical structure (HAS). The term "hollow anatomical structure" is a broad term and is used in its ordinary sense, including, without limitation, veins, arteries, gastric structures, coronary structures, pulmonary structures, tubular structures associated with reproductive organs such as fallopian tubes, uteri, hollow organs and the like. Hollow anatomical structures particularly suited to treatment or occlusion by the methods and apparatus of the disclosed embodiments include veins, such as veins of the lower extremities, for example, veins in the leg, and fallopian tubes.

Figure 1:
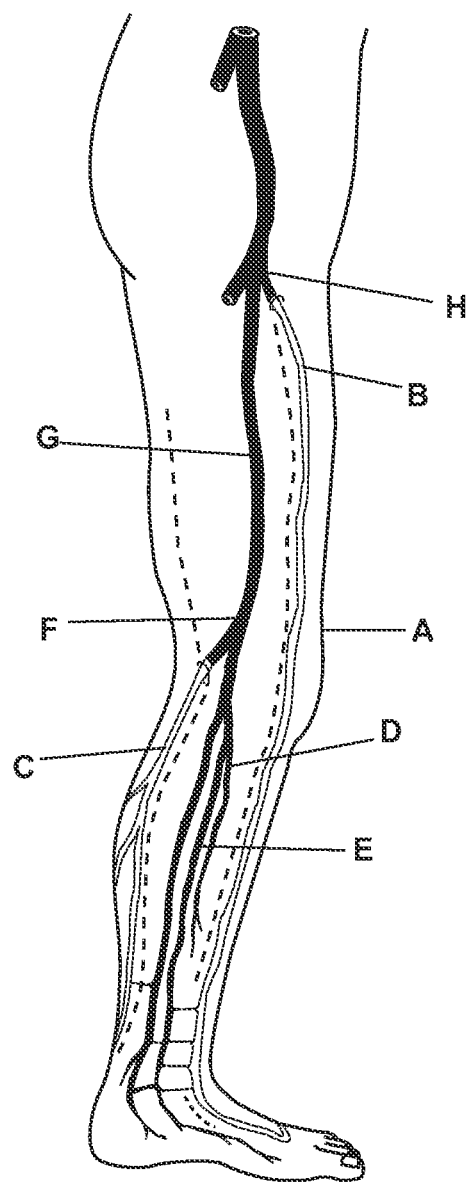
FIG. 1 is a schematic view of a human leg and portions of the deep and superficial venous systems.

Methods, systems, and apparatus for occluding a hollow anatomical structure, such as the veins shown in FIG. 1, in a patient or subject using an implant such as occluding device or occluding material are disclosed. The terms "subject" and "patient" as used herein, refer to animals, such as mammals For example, mammals contemplated by one skilled in the art include humans, primates, dogs, cats, sheep, cattle, goats, pigs, horses, mice, rats, rabbits, guinea pigs, and the like. The terms "subject" and "patient" are used interchangeably.

The terms "occluding device," "occluding implant," and "occluding material" as used herein are broad terms and are used in their ordinary sense, including, without limitation, a substance or device that is capable of occluding or causing occlusion of a HAS. Occluding materials or occluding devices can be formed or fabricated ex situ or formed in situ (e.g., by curing of a prepolymer or uncured polymer). The term "occluding material" as employed herein, includes prepolymers, uncured polymers, unsolidified materials, as well as occluding materials inserted into a patient in polymerized, procured, or solidified form. Biologic materials, e.g., gelatin and thrombin, can also be used separately or in combination with the occlusive materials. Bioresorbable materials are exemplary occluding materials, although other materials can also be used as desired. For example, in one embodiment, the occluding implant can include fibers and/or other components formed from polylactides (PLA) and/or polyglycolides (PGA) or copolymers thereof.

Occluding can include, but is not limited to, blocking by insertion of a plug or other structure into the HAS, such as any one or combination of the veins shown in FIG. 1, that prevents or inhibits flow therethrough, adhering opposite walls of the HAS together so as to prevent or inhibit flow therethrough, compressing the walls of the HAS together so as to prevent or inhibit flow therethrough, or initiating a physiological reaction to an applied force or substance (e.g., energy, chemicals, drugs, physical contact, pressure or the like) that causes flow through the HAS to be inhibited or prevented (e.g., formation of a fibrotic plug or growth of connective tissue). Occlusion can be immediate, or onset of occlusion can be delayed. Occlusion can be partial (i.e., permitting a reduced flow through the HAS) or complete (i.e., permitting no or substantially no flow through the HAS). Occlusion can be permanent or temporary. Occlusion can be affected by resorption characteristics of the material. Occlusion can result in physical change or damage to the HAS (e.g., tissue fibrosis or necrosis) or can block the HAS without substantial physical change (e.g., a biocompatible plug). The mechanisms by which occlusion can occur include but are not limited to formation of an organized fibrotic occlusion resulting from the body's natural foreign body healing response, formation of a wound or damage to tissue, expansion of the occluding device or occluding material, release of a chemical or bioactive agent (e.g., a sclerosant, inflammatory agent, cytokine, growth factor, clotting factor, tissue attachment factor, or other agent) from the occluding device or occluding material, venoconstriction, compression, and ligation.

Figure 2:
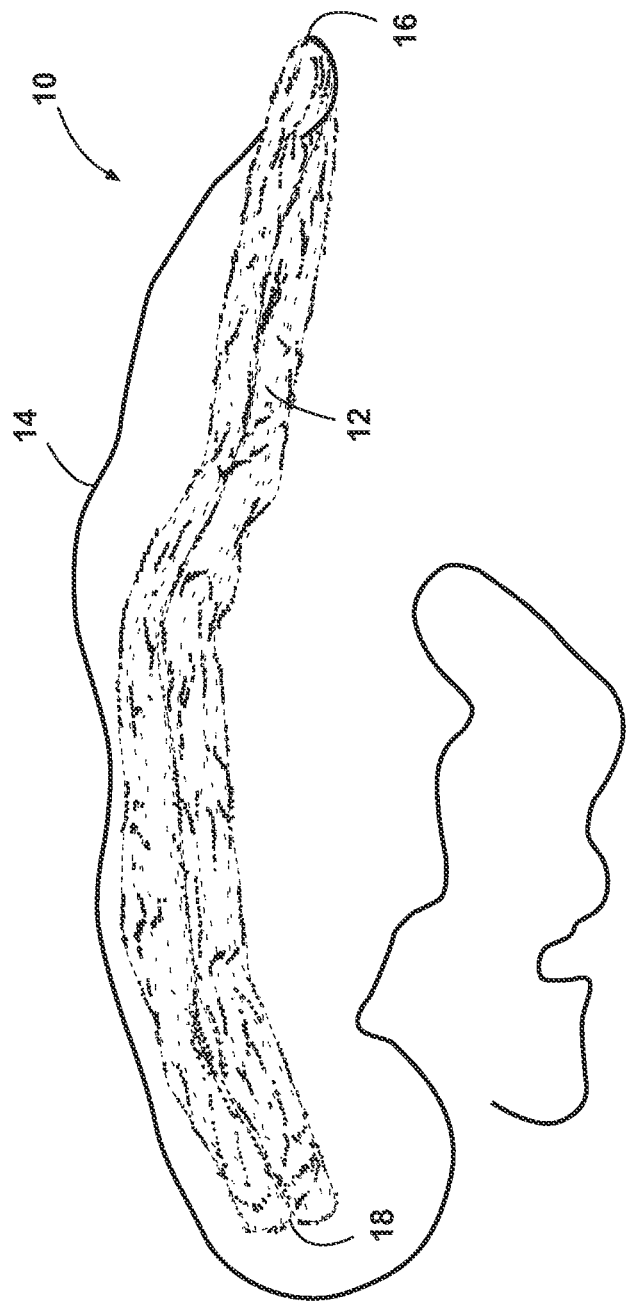
FIG. 2 is an elevation view of an embodiment of an implant for occluding a hollow anatomical structure, such as a vein in the venous systems shown in FIG. 1.

Referring to FIG. 2, an implant 10 according to one embodiment for occlusion of a hollow anatomic structure comprises a bioresorbable body 12. In one embodiment, the body 12 comprises a bioresorbable material in fibrous form, which can comprise a collection of individual fibers that can be spun into multi-filament yarns. The fibers or yarns can be textured to impart bulk. In one embodiment, multiple fibers or yarns can be assembled together to form the body 12. The textured fibers or yarns can be made wavy to prevent adjacent yarns from lying closely together; some fibers or yarns may tangle together. The fibers can be treated and/or agglomerated in any suitable manner to achieve a desired texture, density, geometry, etc. The fibers can be made or treated such that the body 12 can be compressible and/or expandable. For example, as shown in the illustrated embodiment, the body 12 can naturally assume an expanded condition and convert to a compressed condition upon application of a compressive force. Alternatively, the body 12 can naturally assume a compressed condition and convert to an expanded condition upon application of an expansive force. The bioresorbable material can be any suitable bioresorbable material, such as a material from the family of alpha hydroxy acids, for example polylactide (PLA) and/or polyglycolide (PGA).

Suitable forms and materials for the bulked fibrous bioresorbable body (and/or individual yarns or fibers) are disclosed in U.S. Patent Application Publication No. 2006/0212127, published Sep. 21, 2006, and entitled, "Structures for Permanent Occlusion of a Hollow Anatomical Structure," and in U.S. Patent Application Publication No. 2007/0248640, published Oct. 25, 2007, and entitled, "Occlusive Implant and Methods for Hollow Anatomical Structure." Of those publications, the following is incorporated herein by reference: paragraphs 0010-0171 of Publication No. 2007/0248640 and the drawings referenced in those paragraphs.

In the embodiment of FIG. 2, the implant further includes a tether 14 coupled to the body 12. As one example, the body 12 can be generally elongated with a distal end 16 and a proximal end 18, the distance between the distal end 16 and the proximal end 18 (i.e., the length of the body 12) optionally being greater than the cross-sectional diameter of the body 12, and the tether 14 is coupled near or to the distal end 16 of the body 12. The tether 14 can be coupled to the body 12 in any suitable manner, examples of which include tying or stitching the tether 14 to the body 12, employing a coupling agent, such as a bioresorbable or non-bioresorbable adhesive, and making the tether 14 integral with the body 12. In the embodiment of FIG. 2, the tether 14 is coupled to the body 12 by tying the tether 14 around the body 12 near a center of the length of the body 12, and the body 12 is bent or turned where the tether 14 is coupled to the body 12 such that the body 12 is folded upon itself. As a result of this configuration, the coupling location of the tether 14 forms the distal end 16 of the body 12, and the free ends of the body 12 folded upon each other form the proximal end 18 of the body 12. The tether 14 can have any suitable length relative to the length of the body 12. For example, the length of the tether 14 can be greater than, equal to, or less than that of the body 12.

The tether 14 can be bioresorbable and made of the same material as the body 12 or of a material different than that of the body 12. Alternatively, the tether 14 can be non-bioresorbable. Further, the tether 14 can be inelastic or elastic. In the illustrated embodiment of FIG. 2, the tether 14 is made of the same bioresorbable material as the body 12; the body 12 comprises multiple fibers processed and textured such that the body 12 is bulked, elastic, and compressible, and the tether 14 comprises multiple fibers spun into a single, relatively smooth, and inelastic yarn, wherein the cross-sectional diameter of the body 12 in its natural expanded condition is significantly greater than the cross-sectional diameter of the tether 14.

The implant 10 can be positioned in a HAS to occlude the HAS such that blood flow through the HAS is reduced or prevented. While the implant 10 can be positioned in the HAS in any suitable manner, such as the manners disclosed in the above-incorporated material from a patent application publication, additional or alternative techniques and/or apparatus can be employed, as discussed herein.

In one embodiment, the implant body 12 has an overall linear mass density of 7200 denier, and is formed from 48 plies of 75 denier, 30 filament, 100% polyglycolide (PGA) yarns. The PGA material has a molecular weight (Mn) over 12,750 and a polydispersity (PDI) between 1.1 and 1.8. A 30 cm length of the collected 48 plies has a breaking load between 30 and 50 lbf. Among the 48 plies, 24 are "S" twisted and 24 are "Z" twisted, all with a false twist texture of 90 twists per inch. The yarns are false twisted individually using pin twist texturing. The 48 plies are doubled over once at the distal end 16 of the body 12 to create a 7200 denier implant body 12. The tether 14 is formed from 16 plies of 75 denier, 30 filament, 100% polyglycolide (PGA) yarns. The filament denier is 2.5, or about 2.5. All 16 plies are "Z" twisted between 3 and 4 twists per inch and heat set. A 40 cm length of the collected 16 plies has a breaking load between 10 and 17 lbf.

The 48-ply yarn is preferably cleaned by passing it in "reel to reel" fashion through an ultrasonic cleaning bath filled with ≥99% isopropyl alcohol at a temperature maintained below 85 degrees Fahrenheit. The alcohol is replaced at a rate sufficient to clean no more than 100 grams of yarn per gallon of alcohol. After the cleaning bath the yarn is dried by running it past one or more drying air jets.

After cleaning and drying, the yarn can be further bulked by heating. From a supply reel, the yarn is passed through a roller set and then downward in a generally vertical orientation from the roller set, and through a vertically oriented cylindrical heating chamber positioned below the roller set. A takeup reel positioned below and to the side of the lower end of the heating chamber takes up the yarn after it moves through and past the heating chamber. The roller set above the heating chamber pulls the yarn from the supply reel and pushes it downward through the heating chamber. The takeup reel is driven at a speed or speeds that leave the yarn fairly slack between the roller set and the takeup reel, and the yarn passes through the heating chamber in this slack condition so that the filaments separate somewhat for heating. The heating chamber is 4 inches long and 2 inches in inside diameter and the yarn is fed into the heating chamber at a feed speed of 0.0124 meters per second. The heating chamber heats the passing yarn with a circumferential hot air flow directed inwardly at the yarn, which travels approximately along the central vertical axis of the chamber. Air is flowed at a pressure of 60 PSI (+/−5 PSI) through a heater operated at a temperature of 250-350 degrees Fahrenheit, preferably 275 degrees. The heated, pressurized air then flows into the chamber via a circumferential opening or "slit" formed in the chamber inner wall. The temperature inside the chamber, measured at the chamber inner wall next to the circumferential slit (and the incoming airflow) is 155-165 degrees Fahrenheit. The circumferential arrangement of the hot air inflow helps to prevent asymmetric inward airflows which can tend to blow the yarn off axis and induce tension in the yarn and thereby disrupt the bulking.

The dried and heat-bulked yarn can then be cut to the appropriate length (preferably 50 cm) and the tether 14 is tied to the midpoint. The two halves of the yarn are folded against each other to form the implant body 12 with the tether 14 tied at the distal end of the body 12.

The above specified parameters for the implant body 12 and tether 14 can be varied or disregarded in other embodiments. The implant body 12 can have a linear mass density between 6000 and 8000, or between 4000 and 10,000. Between 60 and 120, or between 40 and 140, or between 20 and 200 twists per inch can be employed in texturing the plies/fibers/filaments of the implant body 12. The number and size of the plies can be varied, or a single ply can be employed. Where multiple plies are employed in the body 12, half can be "S" twisted and half can be "Z" twisted. Bioabsorbable materials other than PGA, such as polylactic acid (PLA), or any other suitable bioabsorbable or bioresorbable material specified herein can be employed, either alone or in combination with other such materials. For example, a mixture of PGA and PLA plies/fibers/filaments can be used. Non-bioabsorbable or non-bioresorbable materials can be employed as well. The filament denier in the body 12 can vary between 1.5 and 3.5, or between 0.5 and 5.0, while the filament count can vary between 2000 and 4000, or between 1000 and 5000, or otherwise to fall within the above specified ranges for linear mass density. Where PGA is used in forming the body 12, the molecular weight (Mn) can vary between 10,000 and 15,000, or between 5,000 and 20,000.

FIG. 3 illustrates one embodiment of a system 20 with the implant 10 of FIG. 2, or other suitable implant, and an apparatus 22 configured for storing and/or surgically introducing the implant 10 into a HAS. The depicted apparatus 22 comprises a combined implant storage/introducer unit 24 adapted to store the implant 10 prior to and during introduction of the implant 10 into the HAS, and a sheath assembly 26 coupled with the storage/introducer unit 24 adapted to facilitate introduction of an implant, such as the implant 10, into a HAS. The storage/introducer unit 24 is adapted to feed the implant into the sheath assembly 26 for placement of the implant 10 in the HAS, when manipulated by the practitioner.

The illustrated storage/introducer unit 24 of the depicted embodiment comprises a housing 28 sized to accommodate both the implant 10 and an introducer assembly 30, as will be disclosed in further detail below. The assembled housing 28 comprises a coupler portion 32 for receiving the sheath assembly 26 and coupling the implant 10 with the introducer assembly 30, an introducer portion 34 for accommodating the introducer assembly 30, and an implant storage portion 36 for accommodating the implant 10. In the depicted embodiment, the coupler portion 32 and the storage portion 36 are generally oriented at an obtuse angle relative to each other, and the introducer portion 34 is located approximately at the juncture of the coupler and storage portions 34, 36 such that the storage/introducer unit 24 has an overall "gun-like" configuration.

Figure 5:
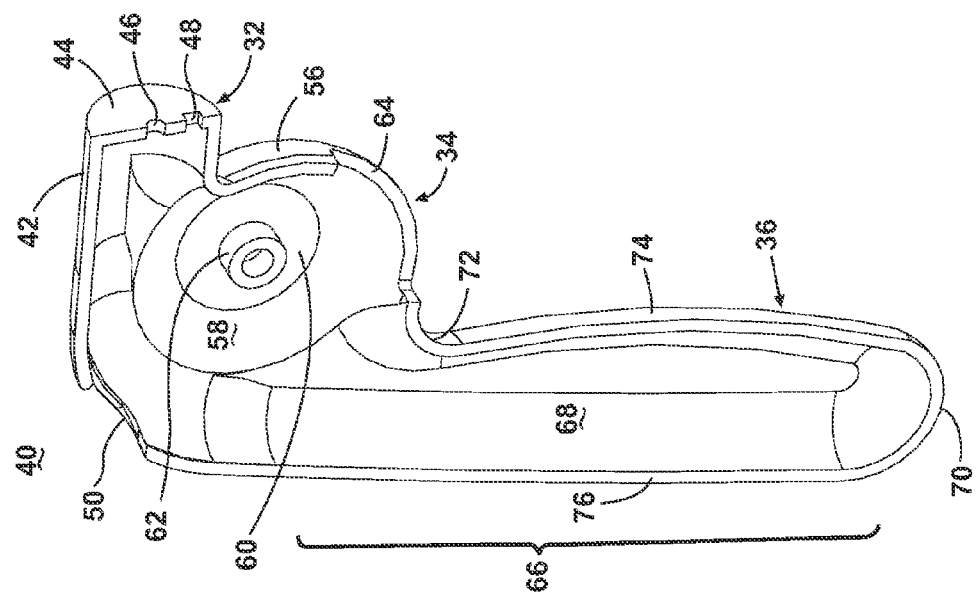
FIG. 5 is a perspective view of a left housing shell of the apparatus of FIG. 3.
Figure 4:
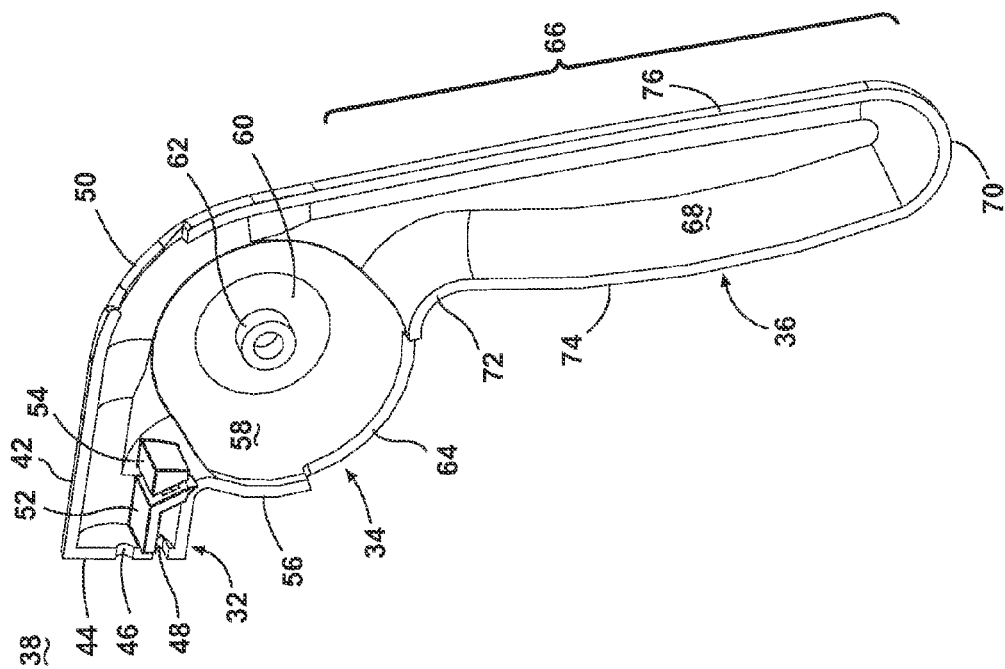
FIG. 4 is a perspective view of a right housing shell of the apparatus of FIG. 3.

Referring to FIGS. 4 and 5, the housing 28 can include a right housing shell 38 and a left housing shell 40 adapted for cooperative registry and defining the coupler, introducer and storage portions 32, 34, 36. In general, the right and left housing shells 38, 40 are contoured, and can be configured with openings, bosses, flanges, and the like, for operational support of the elements comprising the apparatus, and can be molded such that the openings, bosses, flanges, and the like are integrally formed with the right and left housing shells. The right and left housing shells 38, 40 are generally mirror images of each other, and include some, but not all, of the same structural elements.

The coupler portion 32 of the housing 28 is in communication with both the introducer portion 34 and the storage portion 36, and is generally tubular in shape, with a generally cylindrical side wall 42 and a distal or front wall 44 including a first aperture 46 and a second aperture 48 formed by cooperating openings in each of the right and left housing shells 38, 40. The first aperture 46 and the second aperture 48 can be vertically aligned, with the first aperture 46 positioned above the second aperture 48. A third aperture 50 is formed in the side wall 42 at or near the juncture of the coupler portion 32 with the storage portion 36 by cooperating openings in each of the right and left housing shells 38, 40. The coupler portion 32 further includes a cutting guide 52 and a cutting block 54, both of which are provided on the inner surface of the right housing shell 38. The left housing shell 40 does not include a cutting guide or cutting block. Of course, it is within the scope of the present disclosure for the cutting guide 52 and the cutting block 54 to be formed on the left housing shell 40 rather than on the right housing shell 38, or for the cutting guide 52 and the cutting block 54 to be formed by cooperating features on the right and left housing shells 38, 40.

The introducer portion 34 of the housing 28 is generally circular in shape, and includes a curved side wall 56 defining a portion of a circular chamber 58 in communication with the coupler portion 32 and that is formed by the cooperative registry of a circular depression 60 in the side wall of each of the right and left housing shells 38, 40. A hollow cylindrical boss 62 is formed on the inner surface of each of the right and left housing shells 38, 40, in the approximate center of each depression 60. The curved side wall 56 can be continuously formed with the side wall 42 of the coupler portion 32, and includes an elongated slot 64 formed by cooperating openings in each of the right and left housing shells 38, 40.

The storage portion 36 of the housing 28 can be configured to form a handgrip 66 for the apparatus 22 having an inner chamber 68 sized to accommodate the implant 10 extending between a closed end 70 of the handgrip 66 and an open end 72 of the handgrip 66 which is in communication with the coupler portion 32. The handgrip 66 further includes a distal side wall 74 and a proximal side wall 76 extend from the closed end 70, with the distal side wall 74 continuously formed with the curved side wall 56 of the introducer portion 34 and the proximal side wall 76 continuously formed with the side wall 42 of the coupler portion 32.

Figure 6:
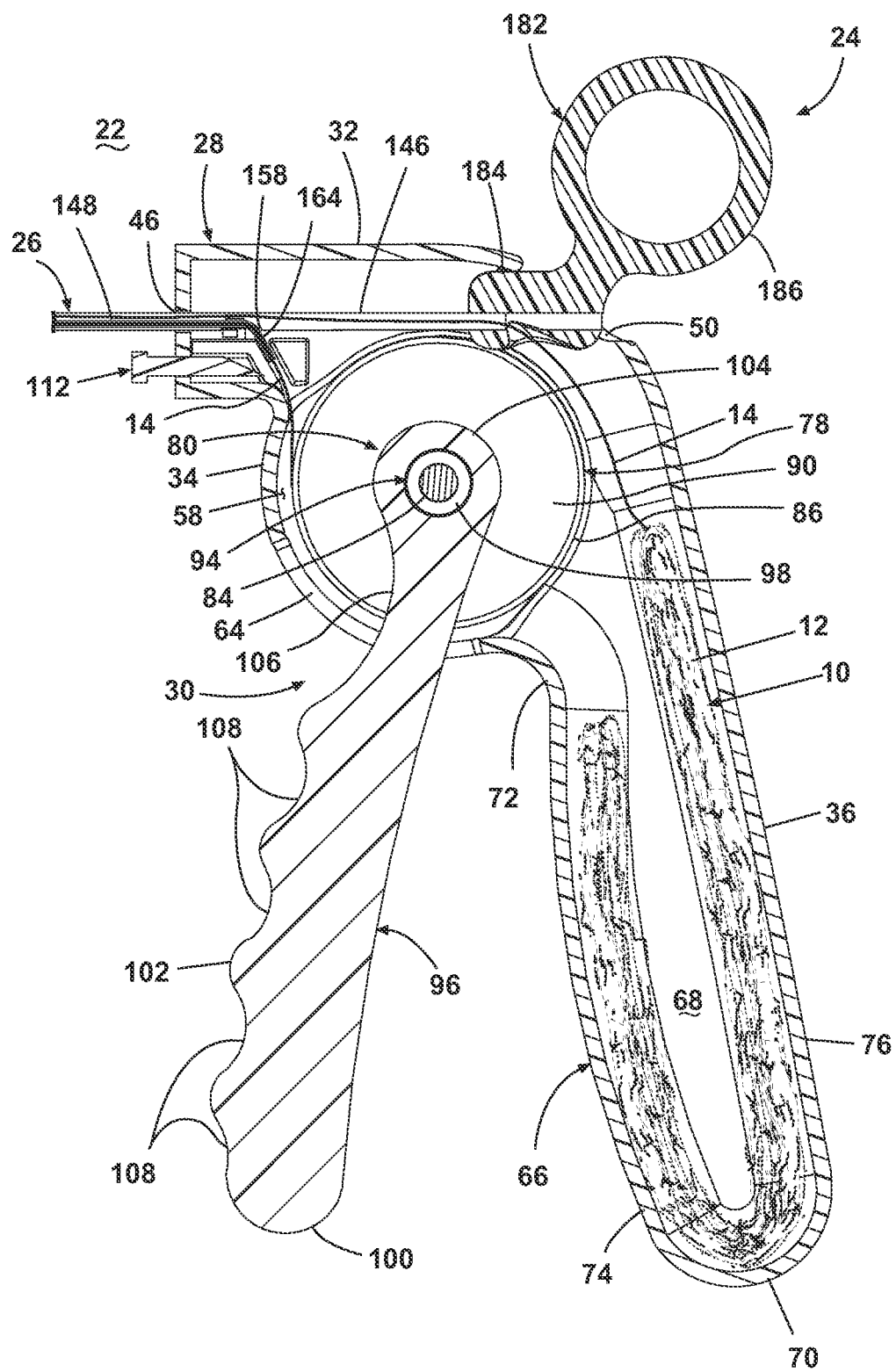
FIG. 6 is a cross-sectional view through the apparatus from FIG. 3 with the apparatus sectioned at line "VI-VI" for clarity.

As shown in FIG. 6, which is a cross-sectional view through the apparatus from FIG. 3 through line "VI-VI", the implant 10 can be stored within the handgrip 66 in a folded manner, with the implant body 12 folded upon itself one or more times. In the embodiment depicted, the handgrip 66 has a sufficient length such that the implant body 12 is folded once within the chamber 68 of the handgrip 66. The interior of the handgrip 66 further is sufficiently wide or spacious to accommodate the folded implant 10 in its natural expanded condition. Alternatively, the interior of the handgrip 66 can be narrow or small enough to compress the implant 10 from its expanded condition to a compressed condition, at any appropriate degree of compression.

Figure 7:
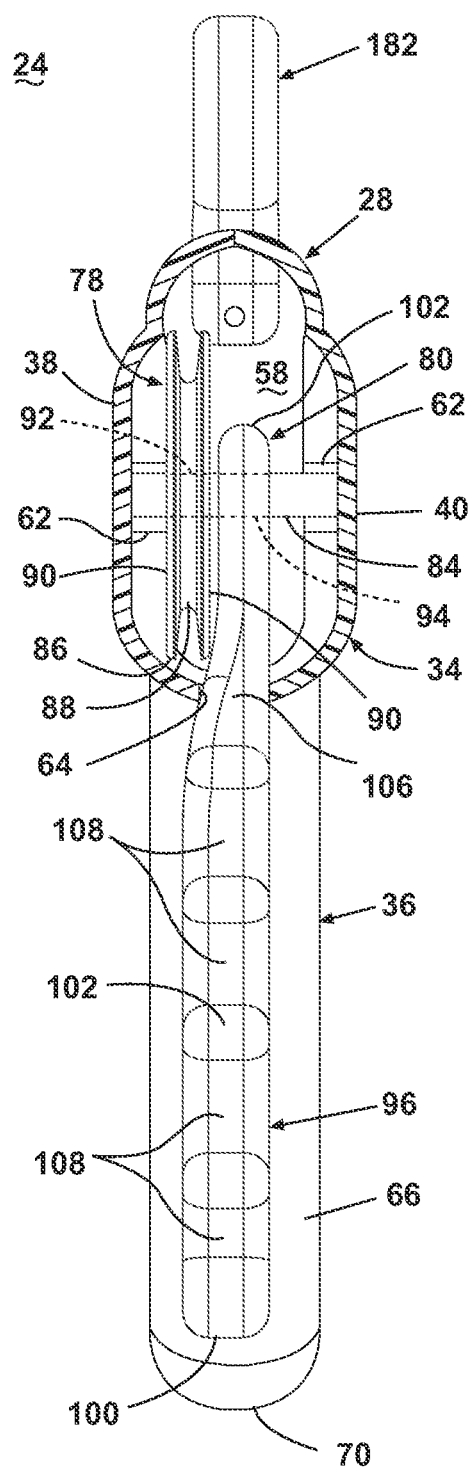
FIG. 7 is a front view of the apparatus of FIG. 3 with the housing sectioned at line "VII-VII" for clarity.

With further reference to FIG. 7, which is a front view of the apparatus of FIG. 3 with the housing 28 sectioned at line "VII-VII" for clarity, the introducer assembly 30 comprises a spool portion 78 around which the tether 14 of the implant 10 can be wound and a reel mechanism 80 coupled to the spool portion 78 for retrieval of the tether 14 from the sheath assembly 26 and to wind the tether 14 onto the spool portion 78, as will be described in greater detail below.

The spool portion 78 includes an axle 84 extending between the bosses 62 formed on the right and left housing shells 38, 40 and a generally flat, circular spool 86 mounted to the axle 84 and received within the chamber 58 of the introducer portion 34 of the housing 28. The axle 84 can be rotatably mounted to the housing shells 38, 40, such that the ends of the axle 84 may rotate within the hollow bosses 62.

The spool 86 includes a barrel 88 between two end flanges 90, with a central bore 92 extending through the barrel 88 and flanges 90. The end flanges 90 have a larger diameter than the barrel 88 to retain the tether 14 when wound around the barrel 88. The bore 92 can receive the axle 84 by a friction fit to fixedly mount the spool 86 to the axle 84; thus, the spool 86 rotates with the axle 84. In another contemplated embodiment, the axle 84 may be fixed with respect to the housing 28, and the spool 86 may rotated relative to the stationary axle 84.

The spool 86 can be offset within the housing 28, such that the spool 86 is primarily received within the depression 60 in the right housing shell 38. The spool 86 can further serve as an anchor for the free end of the tether 14 (e.g. the end of the tether 14 not coupled to the body 12 of the implant 10, as shown in FIG. 2) stored within the apparatus 22. For example, anchoring the free end of the tether 14 to the barrel 88 of the spool 86 ensures that the tether 14 will be wound onto the barrel 88 automatically when the reel mechanism 80 is actuated, as will be described in greater detail below.

The reel mechanism 80 comprises a one-way clutch assembly 94 and an actuator 96 coupled to the clutch assembly 94. The clutch assembly 94 permits the transmission of rotation to the spool 86 in only one direction, and further locks the position of the spool 86 and prevents reverse rotation when the input force from the actuator 96 is removed. In one embodiment, the clutch assembly 94 comprises a one-way needle bearing 98 around the axle 84 that is coupled to the actuator 96 such that movement of the actuator 96 is translated to rotational movement of the needle bearing 98, as will be described in more detail below. One suitable needle bearing 98 is model no. RC02 available from The Timken Co., or part no. 2489K22 available from McMaster-Carr Supply Co.

The depicted actuator 96 comprises a control lever 100 having a grip portion 102 and a ring portion 104 coupled to the grip portion 102 by a neck portion 106. The control lever 100 is received by the introducer portion 34 of the housing 28, with the ring portion 104 received around the axle 84 and the neck portion 106 extending through the slot 64 such that the grip portion 102 is exterior of the housing 28. The slot 64 may be elongated or otherwise sized to accommodate the range of movement of the control lever 100 with respect to the housing 28.

The ring portion 104 receives the needle bearing 98 to couple the control lever 100 to the axle 84, such that rotation of the ring portion 104 causes one-way rotation of the axle 84, thereby causing one-way rotation of the spool 86. The ring portion 104 therefore translates the pivotal movement of the grip portion 102 to rotational movement of the axle 34.

As shown in FIG. 7, the neck portion 106 can be slightly tapered to offset the ring portion 104 from the grip portion 102. The offset ring portion 104 allows space for the spool 85 within the housing 29 while permitting the grip portion 102 to remain relatively centered with respect to the handgrip 66.

The handgrip 66 of the storage portion 36 and the control lever 100 of the introducer portion can be cooperatively shaped to facilitate comfortable gripping of the storage/introducer unit 24 with a single hand of a practitioner. As illustrated, the grip portion 102 includes grip features 108 to facilitate handling of the apparatus 22 by a practitioner. Particularly, the grip features 108 may be ergonomically shaped or otherwise formed to facilitate gripping the control lever 100 with one or more fingers of a single hand of the practitioner. The handgrip 66 can further be ergonomically shaped or otherwise formed to facilitate gripping the handgrip 66 with the palm and thumb of the same single hand of the practitioner. The apparatus 22 can be gripped according to the practitioner's preference, such as with a single hand wrapped around the handgrip 66 and the control lever 100, with some or all of the fingers of the single hand engaged with the grip features 108 on the control lever 100 and the palm and thumb of the same single hand engaged with the handgrip 66, although other gripping arrangements or techniques are possible. Further, the handgrip 66 and the control lever 100 can be shaped to facilitate an equally comfortable gripping of the apparatus 22 by a left-handed practitioner or a right-handed practitioner.

Depression of the control lever 100, i.e. squeezing the control lever 100 toward the handgrip 66 of the housing 28, causes the spool 86 to rotate in a counterclockwise direction, per the orientation shown in FIG. 6, by way of the needle bearing 98 between the control lever 100 and the axle 84. Rotation of the spool 86 draws a length of the tether 14 onto the barrel 88, which advances the implant 10 distally through the apparatus 22, as will be described in further detail below. In some embodiments, an electric motor (not shown) can be employed to rotate the spool 86, in place of the control lever 100, etc.; in such embodiments the motor can be powered by an onboard battery and actuated by a trigger switch or the like located on or near the handgrip 66.

While not illustrated herein, the storage/introducer unit 24 can be provided with a safety feature to prevent unwanted or inadvertent actuation of the introducer assembly 30 to avoid accidental advancement of the implant 10. For example, the actuator 96 can be provided with a safety lock that must be removed or unlocked before the control lever 100 can be depressed.

Figure 8:
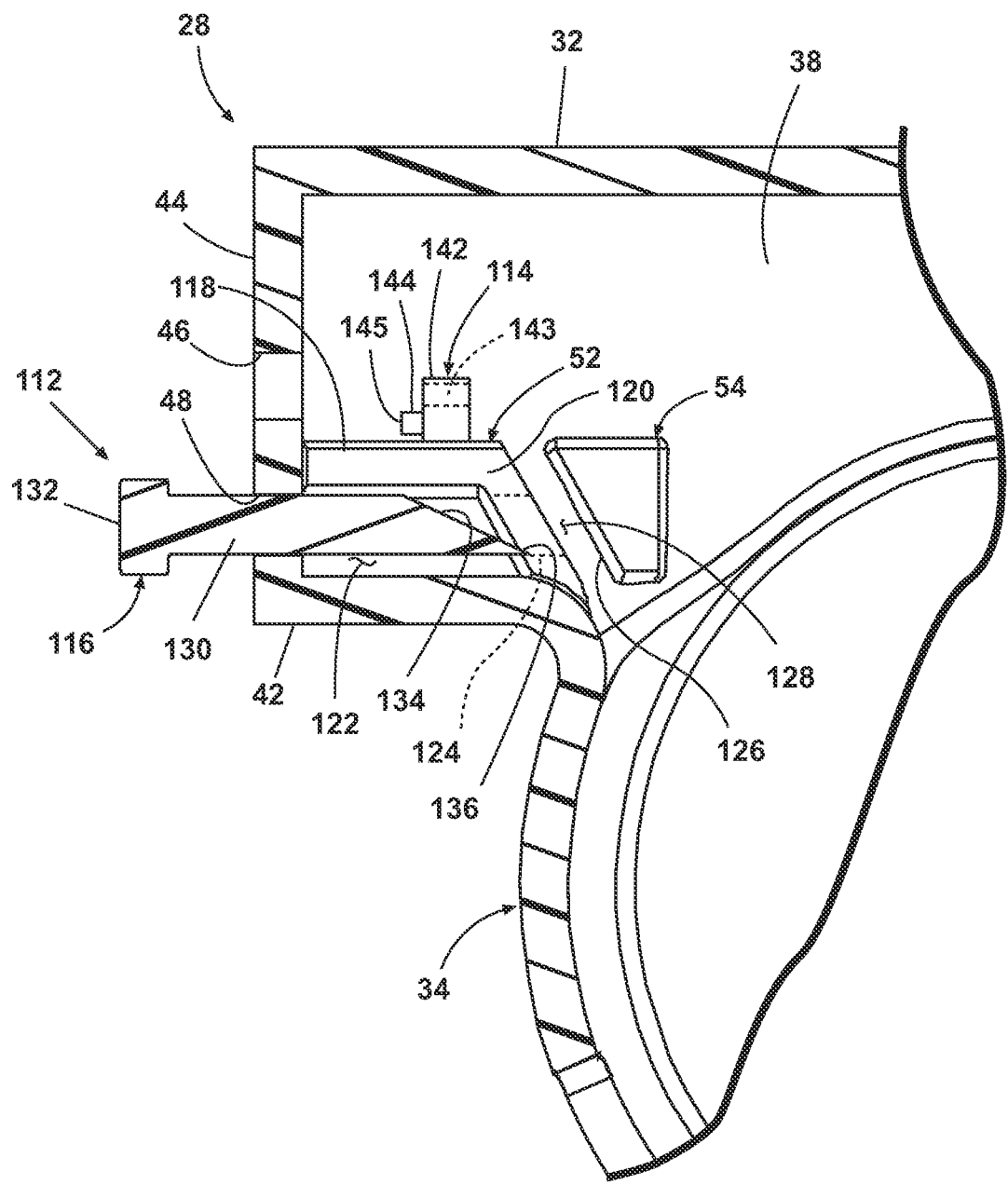
FIG. 8 is a close-up view of a portion of FIG. 6 to illustrate a tether cutting assembly and a sheath cutting assembly of the apparatus; a sheath assembly and the implant are not shown for clarity.

Referring to FIG. 8, which is a close-up view of a portion of FIG. 6 with the inner and outer sheaths 148, 146 and implant 12 not shown for clarity, the coupler portion 32 houses a tether cutting assembly 112 and a sheath cutting assembly 114. The tether cutting assembly 112 includes the cutting guide 52 and cutting block 54 formed on the right housing shell 38, as well as a moveable cutting actuator 116 which is guided by the cutting guide 52 and which engages the cutting block 54 to sever the tether 14 of the implant 10, as will be described in greater detail below.

The cutting guide 52 includes an upper wall 118 and an angled rear wall 120. The upper wall 118 is joined at one end to the front wall 44 of the coupler portion 32 and at the opposite end to the angled rear wall 120, which is in turn joined to the side wall 42; the walls of the cutting guide 118, 120 and the coupler portion 32 thereby form a substantially enclosed guide channel 122. The guide channel 122 extends between an aperture 124 formed in the angled rear wall 120 and the lower second aperture 48 in the front wall 44 of the coupler portion 32. The aperture 124 in the angled rear wall 120 is generally aligned with and in communication with the lower aperture 48 in the front wall 44.

The cutting block 54 includes a cutting surface 126 in opposed relation to the aperture 124 of the cutting guide 52. In the depicted embodiment, the cutting surface 126 is generally parallel to and spaced from the rear wall 120 of the cutting guide 52. The space between the cutting surface 126 and the rear wall 120 defines a channel 128 in communication with the introducer portion 34 of the housing 28.

The cutting actuator 116 has an elongated shaft 130 with a trigger button 132 at the distal end of the shaft 130 and a cutting element 134 at the proximal end of the shaft 130. As depicted, the cutting element 134 can be formed as an angled cutting edge 136 on the terminal end of the shaft 130. The shaft 130 can be received within the channel guide 122, with a portion of the shaft 130 projecting through the lower second aperture 48 on the front wall 44, such that the trigger button 132 is on the exterior of the housing 28, and the cutting element 134 is aligned with the aperture 124. In one embodiment, the cutting actuator 116 is biased to a position in which the cutting element 134 is spaced from the cutting surface 126 by a biasing element (not shown).

While not illustrated herein, the apparatus 22 can be provided with a safety feature to prevent unwanted or inadvertent actuation of the tether cutting assembly 112 to avoid accidentally cutting the tether 14. For example, tether cutting assembly 112 can be provided with a safety lock that must be removed or unlocked before the cutting actuator 116 can be depressed.

The sheath cutting assembly 114 includes a blade holder 142 extending from the upper wall 118 of the cutting guide 52 and having a through-opening 143 formed therein. A blade 144 is supported by the blade holder 142 below the through-opening 143. The blade 144 may include a wedge-shaped tip 145. In one embodiment, the tip 145 may be sharpened or otherwise formed as a cutting tip.

Referring to FIG. 9, the illustrated sheath assembly 26 includes an outer sheath 146 and an inner sheath 148. At least a portion of the inner sheath 148 can be received by the outer sheath 146. The outer sheath 146 has a tubular and flexible shaft 150 defining a lumen 152, and having an open distal end 154 and an open proximal end 156. An aperture 158 may be formed in the sidewall of the shaft 150, between the distal and proximal ends 154, 156; as illustrated, the aperture 158 can be formed closer to the proximal end 156 than the distal end 158. The outer sheath 146 can be formed from materials suitable for use in the construction of standard introducer sheaths, including Pebax, HDPE, FEP, PTFE, or nylon. The outer sheath 146 can be sized for insertion into a HAS; as an example, the outer sheath 146 can be 8 French with an outer diameter of about 3.38 mm and inner diameter of about 2.79 mm, and a length of about 55 cm measured from the distal end of the storage/introducer unit 24. The outer sheath 146 can further be sized for receipt of the body 12 of the implant 10.

The inner sheath 148 has a tubular and flexible shaft 160 defining a lumen 162. The inner sheath 148 can be sized for receipt within the lumen 152 of the outer sheath 146; as an example, the shaft 160 of the inner sheath 148 can have an outer diameter of about 1.10 mm and an inner diameter of about 0.72 mm. The inner sheath 148 can further be sized for receipt of the tether 14 of the implant 10. The inner sheath 148 can comprise a metallic (e.g. stainless steel such as type 304 stainless steel) tube or hypotube with the distal end thereof formed into the pulley feature 172. However, any suitable member can be employed as the inner sheath 148 that has sufficient column strength to hold the pulley feature 172 in position against the tension in the tether 14 as the implant body 12 is drawn distally. For example, a solid (lumen-less) rod with the pulley feature 172 or similar structure at the distal end thereof can be employed in place of the inner sheath 148; where such a rod is employed, the portion of the tether 14 that would otherwise reside in the inner sheath lumen can extend alongside the rod within the outer sheath lumen.

As shown, the shaft 160 of the inner sheath 148 terminates in a proximal end region 164 and a distal tip region 166. The proximal end region 164 extends through the aperture 158 of the outer sheath 146 and includes an open proximal end 168 of the shaft 160. The proximal end region 164 curves and/or angles away from the longitudinal axis of the shaft 160 in order to pass through the aperture 158 in the side wall of the shaft 150 of the outer sheath 146. As illustrated, the distal tip region 166 can be flush with or proximally of the open distal end 154 of the shaft 150. Alternatively the distal tip region 166 can project distally of the outer sheath 146 by a short distance.

With additional reference to FIG. 10, which is an enlarged perspective view of the distal tip region 166 of the inner sheath 148 (with the tether 14 and the outer sheath 146 not shown for clarity), the distal tip region 166 includes an distal opening 170 providing access to the lumen 162 and a bearing surface or pulley feature 172 which changes or reverses the direction of the force applied by the introducer assembly 30 on the implant body 12 via the tether 14, as will be described in greater detail below. The distal opening 170 can be formed at the distal terminal end of the shaft 160. The pulley feature 172 defines a pulley lumen 174 having a distal opening which forms an inlet opening 176 to the pulley lumen 174 and a proximal opening which forms an outlet opening 178 from the pulley lumen 174. The pulley lumen 174 is in communication with the lumen 162 of the inner sheath 148 via the inlet opening 176. In the depicted embodiment, the pulley feature 172 is foamed by a semi-circular arched wall 180 that is open at its outer side, thus providing an open pulley lumen 174; however, the pulley feature 172 can alternately be closed to form an enclosed pulley lumen. The opening at the outer side of the wall 180 is generally continuous with the distal opening 170 of the shaft 160. The arched wall 180 can have a semi-circular shape to help retain the tether 14 within the pulley lumen 174 when tension is applied to the tether 14. Instead of the depicted pulley 172, a rounded (e.g. cylindrical or hemi-cylindrical) bar or tube can be disposed at the distal end of the inner sheath 148 and oriented orthogonal to the longitudinal axis of the inner sheath 148, such that a curved distal surface of the bar or tube faces distally and away from the inner sheath 148. Such a curved distal surface can act as a bearing surface or pulley surface over which the direction of travel of, and tension in, the tether 14 is changed or reversed. A groove or V-shaped channel can be formed in such a bearing/pulley surface to prevent the tether 14 from slipping off the surface during use. In its various forms, the bearing surface or pulley feature 172 can be located at or near the distal end of the outer sheath 146, within the lumen 162 of the outer sheath 148 as depicted, or partially or completely distal of the outer sheath 148, in which case the bearing surface or pulley feature 172 can be aligned with the lumen 162 (e.g. not protruding radially outward beyond a distal projection of the lumen 162).

As shown in FIG. 9, the tether 14 extends through both the outer sheath 146 and the inner sheath 148 for cooperative movement during advancement of the sheath assembly 26. In the illustrated embodiment, the tether 14 extends from the spool 86 (FIGS. 6, 11) and enters the lumen 162 of the inner sheath 148 through the open proximal end 168 of the shaft 160. The tether 14 extends through lumen 162 and passes into the pulley lumen 174 of the pulley feature 172 through the inlet opening 176. The tether 14 then reverses direction over the pulley feature 172 and passes out of the pulley lumen 174, through the outlet opening 178 and into the lumen 152 of the shaft 150 of the outer sheath 146, and thereafter passes out of the outer sheath 146 via the open proximal end 156 of the shaft 150.

Figure 11:
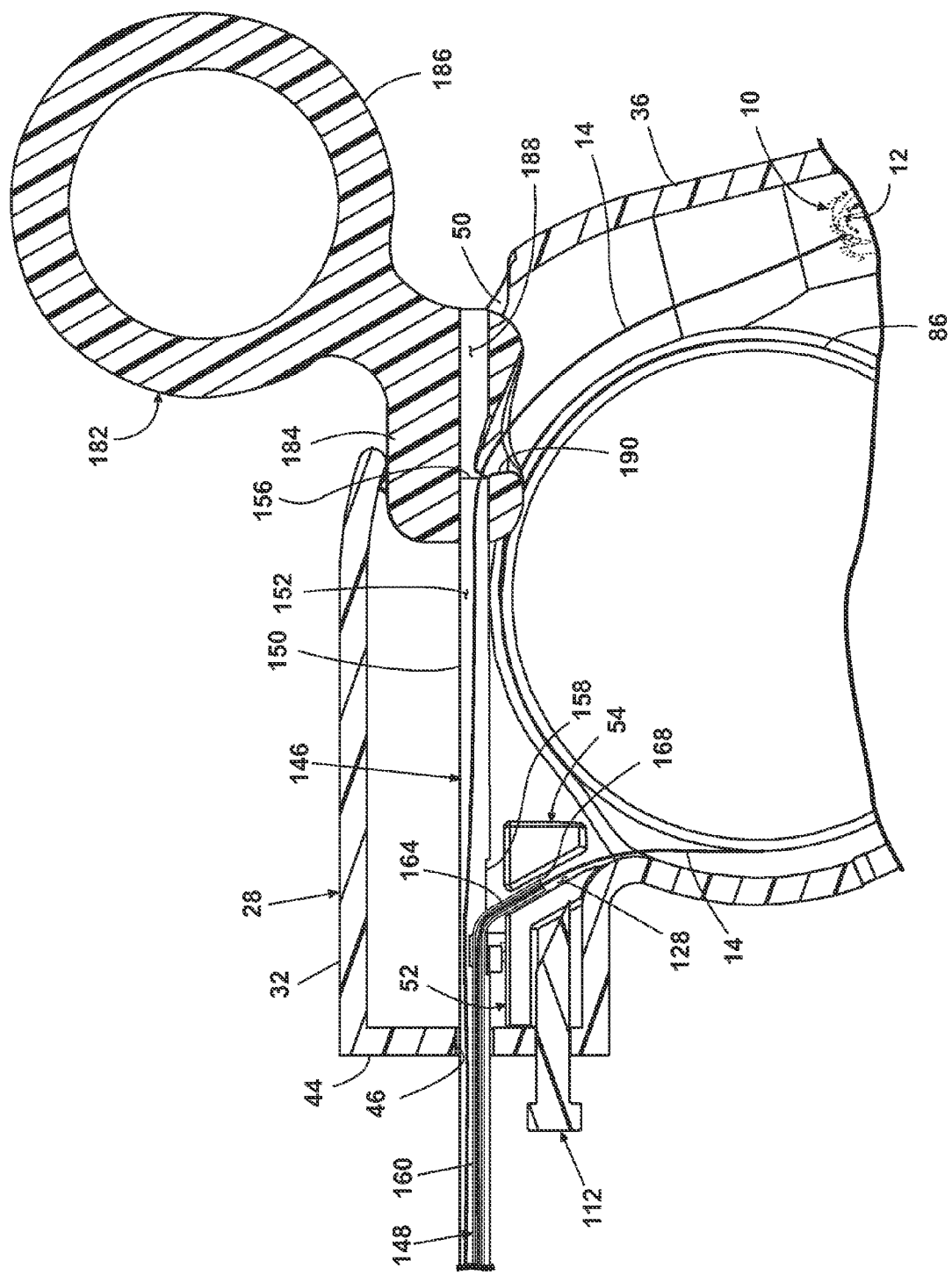
FIG. 11 is a close-up cross-sectional view through the apparatus from FIG. 3 to illustrate the assembly of the sheath assembly from FIG. 8 with the housing of the apparatus from FIG. 3 and the path of the tether of the implant of FIG. 2 through the housing.

Referring to FIG. 11, which is a close-up cross-sectional view through the apparatus 22 from FIG. 3, a handle 182 for the outer sheath can be provided as illustrated, The handle 182 includes a hub 184 attached to a proximal end of the shaft 150 of the outer sheath 146 and a circular grip 186 projecting from a proximal portion of the hub 184, generally at an angle with respect to the longitudinal axis of the outer sheath 146. The circular grip 186 can be formed with or attached to the hub 184.

The hub 184 comprises an opening 188 which receives the shaft 150 to mount the outer sheath 146 to the handle 182, and a side port 190 extending from the opening 188. The side port 190 is in communication with the lumen 152 of the outer sheath 146 via the open proximal end 156. The side port 190 can be tapered such that the cross-sectional area of the side port 190 decreases in a direction toward the shaft 150. This tapering facilitates the compression of the implant 10 as it enters the outer sheath 146 through the side port 190, as will be described in more detail below.

The handle 182 is received by the coupler portion 32 of the housing 28, with the hub 184 projecting through the third aperture 50 formed at or near the juncture of the coupler portion 32 with the storage portion 36 of the handle 28 such that the circular grip 186 is exterior of the housing 28. The outer sheath 146 projects distally from the opening 188 in the hub 184 and passes through the upper first aperture 46 in the front wall 44 of the coupler portion 32. In this position, the outer sheath 146 is aligned with the sheath cutting assembly 114. Particularly, the shaft 150 of the outer sheath 146 is adjacent to and/or engaged with the blade 144 of the sheath cutting assembly 114, such that the tip 145 will cut the side-wall of the shaft 150 as the outer sheath 146 is withdrawn from the housing 28, as will be described in greater detail below. In an alternate embodiment, the shaft 150 of the outer sheath 146 can be precut, and the blade 144 of the sheath cutting assembly 114 may function to simply part the precut shaft 150 to clear the inner sheath 148 as the outer sheath 146 is withdrawn from the housing 28 rather than create a new cut in the shaft 150.

The inner sheath 148 extends through the outer sheath 146, with the proximal end region 164 extending through the aperture 158 of the outer sheath 146 and into the channel 128 between the cutting guide 52 and the cutting block 54 such that the open proximal end 168 of the shaft 160 of the inner sheath 148 is in communication with the channel 128. The shaft 160 of the inner sheath 148 further passes through the through-opening 143 formed in the blade holder 142 of the sheath cutting assembly 114, which helps to maintain the position of the inner sheath 148 with respect to the housing 28 as the outer sheath 146 is withdrawn from the housing 28, as will be described in greater detail below.

The tether 14 of the implant 10 extends from the spool 86 and passes through the channel 128 between the cutting guide 52 and the cutting block 54 to enter the open proximal end 168 of the shaft 160 of the inner sheath 148. The tether 14 then follows the path through the introducer assembly 26 shown in and described with respect to FIGS. 9 and 10. The portion of the tether 14 that passes out of the open proximal end 156 of the shaft 150 of the outer sheath 146 exits the hub 184 through the side port 190, and joins the implant body 12 stored within the chamber 68 of the handgrip 66, as shown in and described with respect to FIG. 6.

While not illustrated, the apparatus 22 can further be provided with a safety feature to prevent unwanted or inadvertent withdrawal of the outer sheath 146 from the housing 28. For example, the handle 182 can be provided with a safety lock that must be removed or unlocked before the handle 182 can be moved relative to the housing 28.

During the storage and introduction of the implant 10, the implant body 12 assumes multiple conditions with respect to the expansion and compression of the implant body 12. FIGS. 12-15 illustrate sectional views of the implant body 12 in the exemplary conditions. As examples, the implant body 12 in the illustrated embodiment assumes an unstressed or "natural" expanded condition when in the handgrip 66 of the storage portion 36 of the apparatus 22 during storage (e.g., a storage condition, FIG. 12), a first compressed condition when in the outer sheath 146 of the sheath assembly 26 during introduction (e.g., a first introduction condition, FIG. 13), a second compressed condition when in the outer sheath 146 adjacent the inner sheath 148 of the sheath assembly 26 during introduction (e.g., a second introduction condition, FIG. 14), and, assuming the HAS has a differing cross-sectional diameter than the outer sheath 146 with or without the inner sheath 148, a third compressed condition when in the HAS, shown as the greater saphenous vein B for illustrative purposes, after implantation (e.g., an implantation condition, FIG. 15). The implant body 12 also undergoes transitional conditions when converting between the storage, first introduction, second introduction, and implantation conditions. These conditions can be imposed on the implant body 12 because of the cross-sectional diameter of the structure that houses the implant body 12; once the housing structure cross-sectional diameter is sufficient to cause compression of the implant body 12, compression of the implant body 12 increases as the housing structure cross-sectional diameter decreases. The housing structures corresponding to the storage, first introduction, second introduction, and implantation conditions of the illustrated embodiment are, respectively, the handgrip 66 of the implant storage portion 36, the shaft 150 of the outer sheath 146 without and with the inner sheath 148 extending through the lumen 152 of the shaft 150, and the HAS, in this case, the greater saphenous vein B.

Embodiments of methods of use of the system 20 are described below. While the system 20 can be employed in conjunction with any suitable HAS, the methods are described with respect to the greater saphenous vein B for illustrative purposes. It will be understood that the methods can be modified or adapted as necessary, if necessary, for use in other HASs. The methods can also be modified or adapted as necessary, if necessary, for use with embodiments of the system 20 other than the embodiment employed in the following description. In the description of the methods, various steps are discussed in terms of being performed by the practitioner using a single hand; however, it is understood that these steps may be performed by the practitioner using both hands or by alternating hands. It is assumed that prior to the embodiment of the method of use of the system 20 described below, that the implant 10 is stored within the apparatus 22 as described and shown in the preceding figures; including the implant body 12 of the implant 10 stored within the handgrip 66 and the tether 14 of the implant 10 passing from the handgrip 66, though the sheath assembly 26 and to the spool 86 of the introducer assembly 30. The tether 14 of the implant 10 is thereby coupled between the implant body 12 and the spool 86.

In one embodiment of a method of use of the system 20, various stages of which are depicted in FIGS. 16-29, the target HAS (e.g., a vein such as the greater saphenous vein B) can first be accessed at an access site through the skin by using a suitable access technique (e.g., the Seldinger technique). In one example, the vein B is punctured with a hollow access needle, optionally under ultrasonic guidance, and a guidewire is passed into the vein B through a lumen of the needle. The needle is then withdrawn, and the sheath assembly 26 is fed over the guidewire into the vein B and advanced to the desired implant location. In the case of the greater saphenous vein B, the desired implant location is just below the sapheno-femoral junction H. The guidewire is then withdrawn from the sheath assembly 26, thereby leaving the sheath assembly 26 or a portion thereof in the vein B. The position of the sheath assembly 26 relative to the vein B and the sapheno-femoral junction H can be verified using appropriate techniques, such as ultrasound imaging. Optionally, a dilator can be employed with the system 20 to feed the sheath assembly 26 over the guidewire. The dilator is inserted into the lumen 152 of the shaft 150 through the open distal end 154 in the space between the sidewall of the shaft 150 and the inner sheath 148. In one embodiment, the dilator can include a flattened side to account for the inner sheath 148 within the outer sheath 146.

Figure 16:
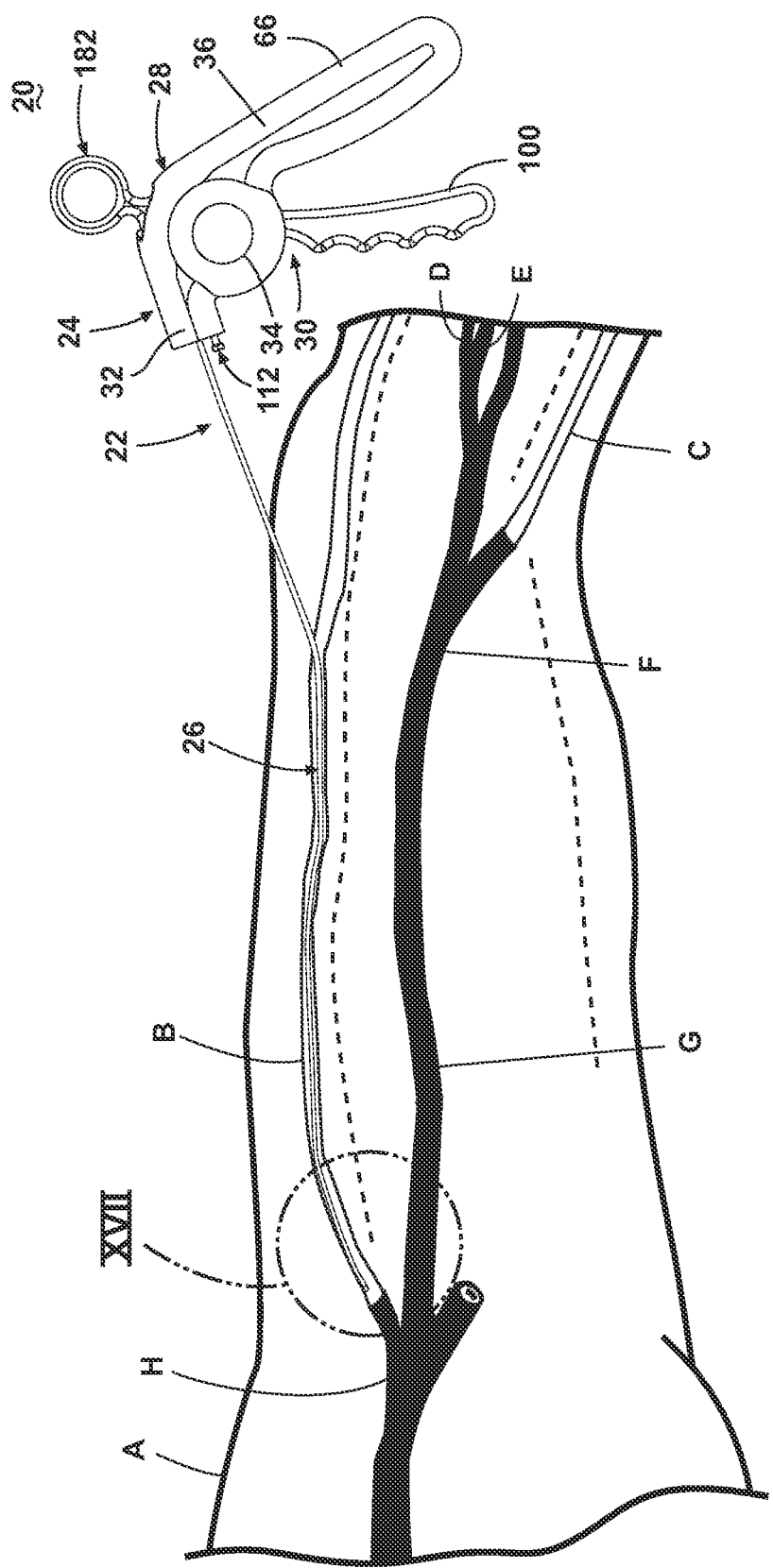
Figure 17:
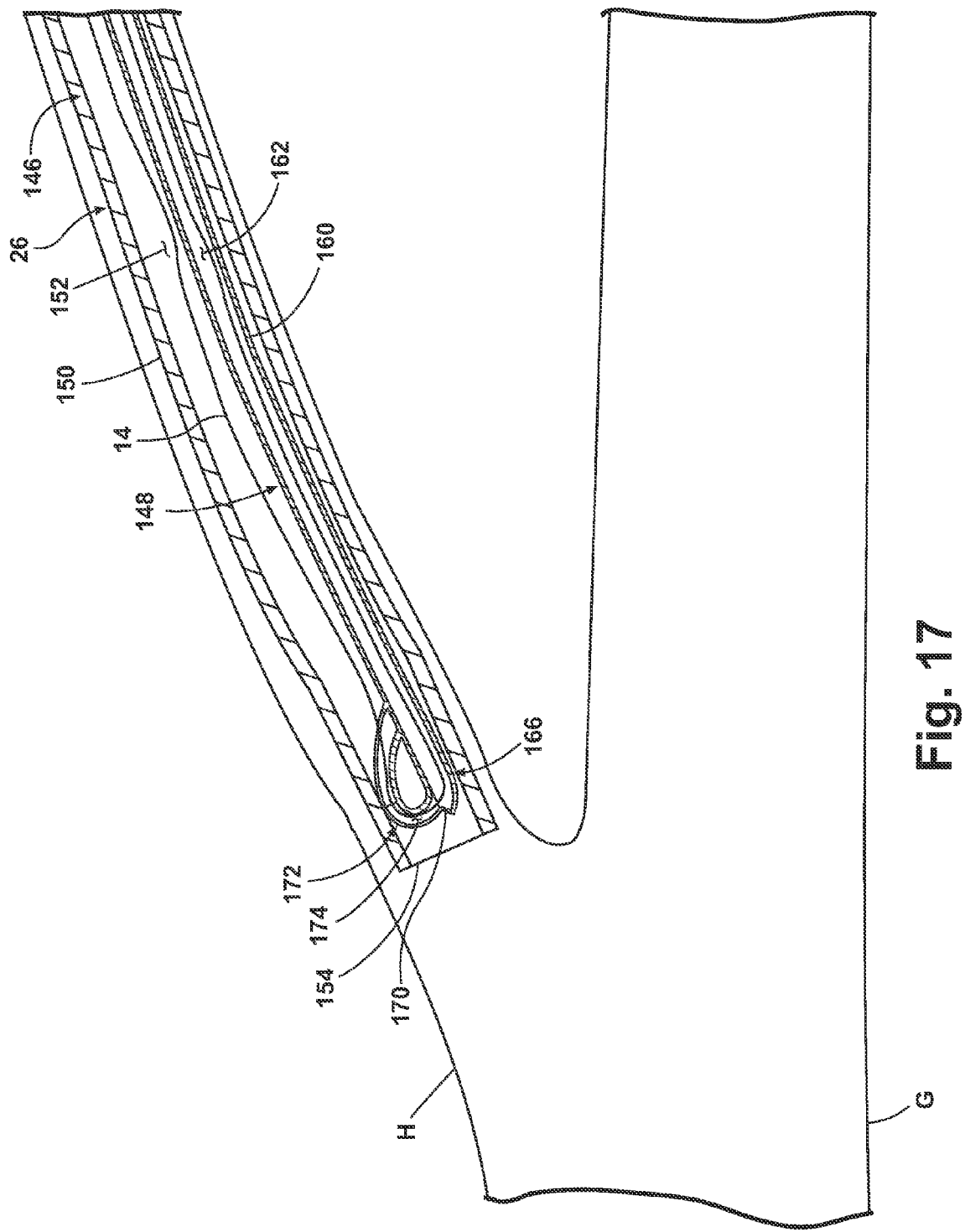
Figure 18:
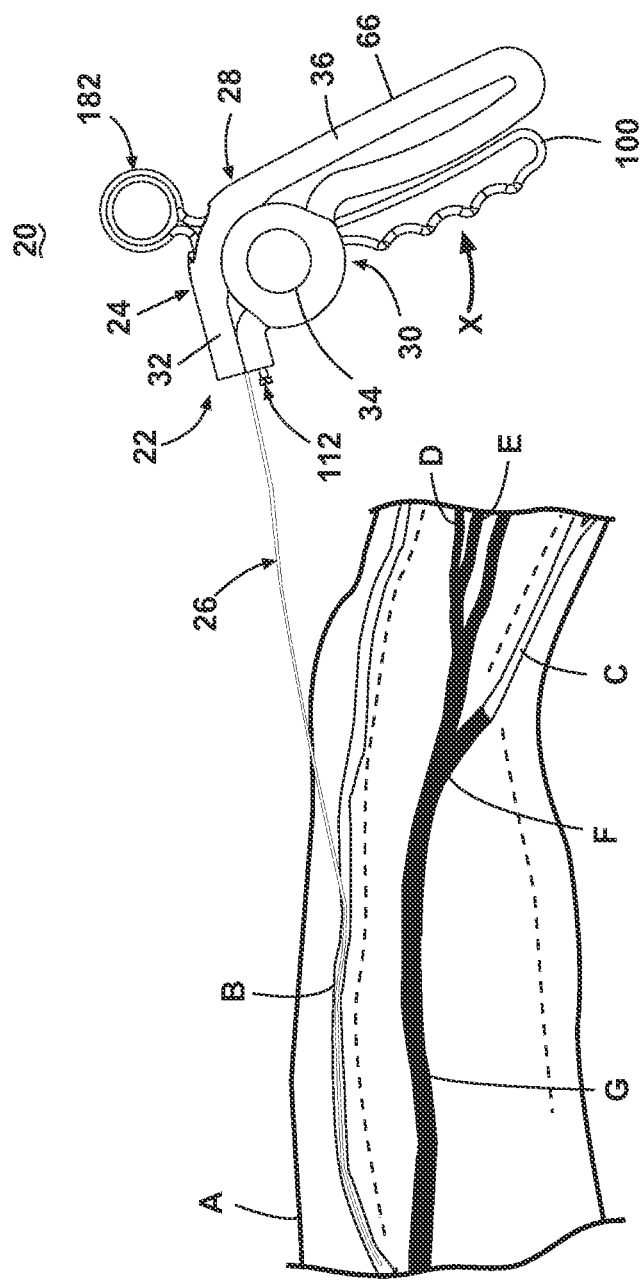

FIG. 16 illustrates the leg A with the sheath assembly 26 located in the greater saphenous vein B and the storage/introducer unit 24 positioned externally of the leg A. FIG. 17 provides an enlarged view of the region labeled "XVII" in FIG. 16 to show the location of the distal portion of the sheath assembly 26, including the distal tip region 166 of the inner sheath 148, in the saphenous vein B and relative to the sapheno-femoral junction H.

When the apparatus 22 is oriented as desired, the practitioner can optionally remove a safety feature (not shown) preventing unwanted or inadvertent actuation of the introducer assembly 30; the apparatus 22 in this state is ready for introduction of the implant 10 into the vein B. The practitioner grasps the handgrip 66 and the control lever 100 and begins to reel in the tether 14 by applying a proximal force to the control lever 100 to effectively squeeze the control lever 100 toward the handgrip 66 of the housing 28, as illustrated by the arrow X in FIG. 18, thereby advancing the implant 10 out of the implant storage portion 36 and through the coupler assembly 32. In particular, depressing the control lever 100 causes the spool 86 to rotate by way of the needle bearing 98 between the control lever 100 and the axle 84. Rotation of the spool 86 draws a length of the tether 14 onto the barrel 88. This shortens the effective length of the tether 14, which can be defined as the unwound length of the tether 14 between the spool 86 and the distal end 16 of the implant body 12.

Figure 19:
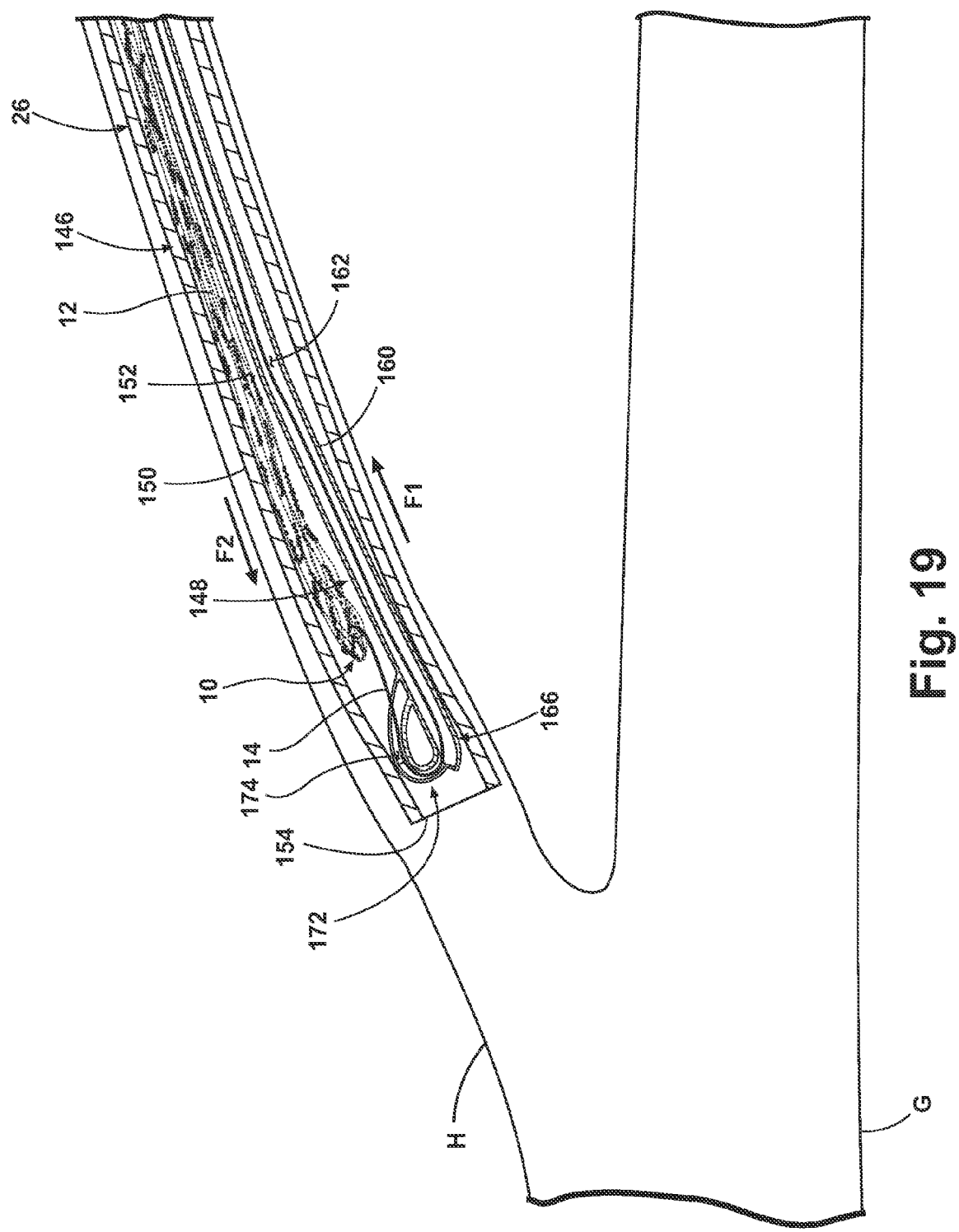

With reference to FIG. 19, the shortening of the effective length of the tether 14 pulls the implant body 12 distally through the outer sheath 146 by virtue of the pulley feature 172, which changes the direction of the force applied by the introducer assembly 30 on the implant body 12 via the tether 14. Specifically, the pulley feature 172 changes the force of the tether 14 from a proximally-directed force F1 within the inner sheath 148 to a distally-directed force F2 within the outer sheath 146.

Figure 20:
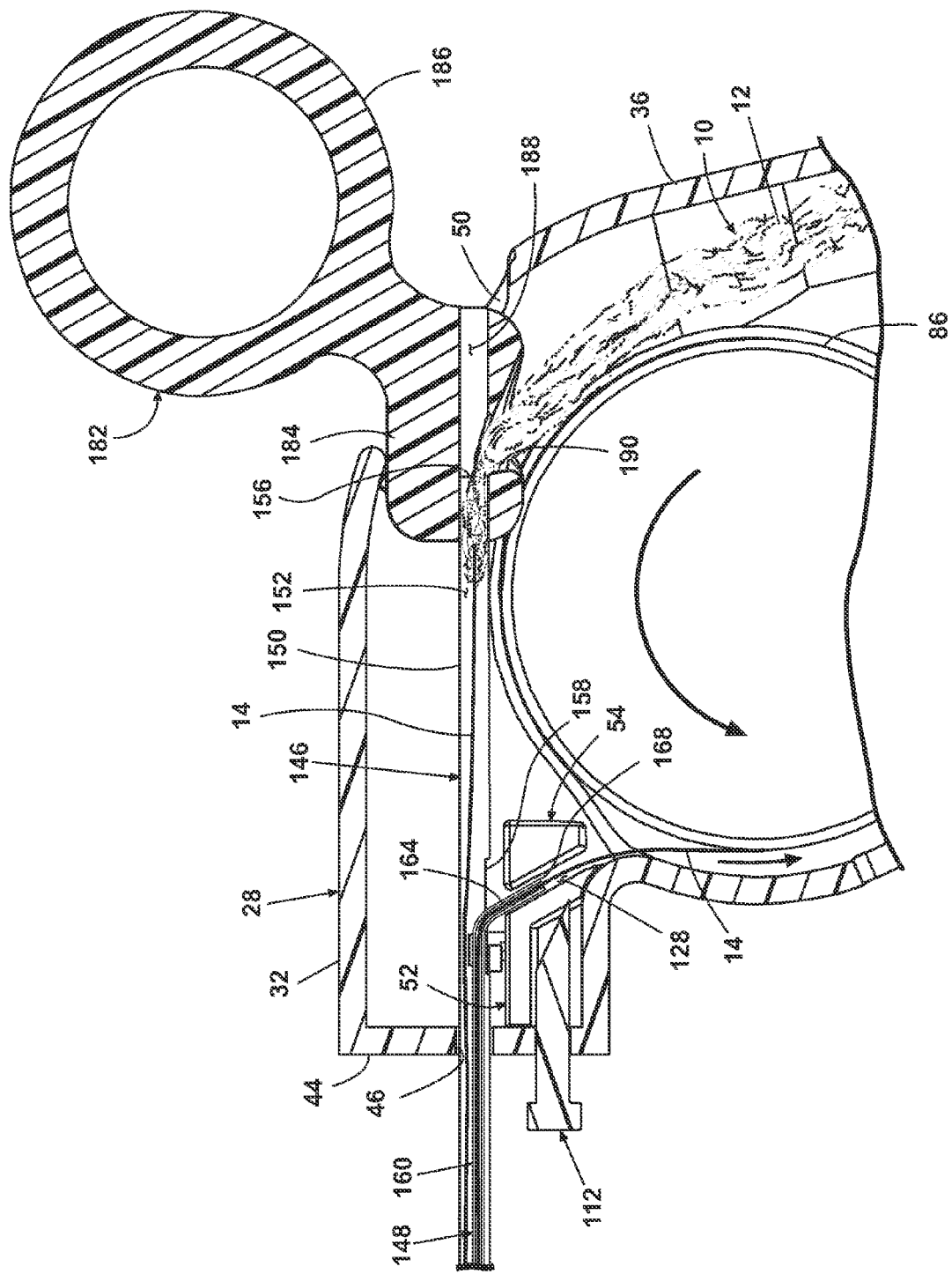

As depicted in FIG. 20, the force of the tether 14 on the implant body 12 pulls the implant body 12 distally through the side port 190 in the hub 184 of the handle 182 to enter the open proximal end 156 of the shaft 150 of the outer sheath 146. After entering the open proximal end 156, the implant 10 continues its advancement through the lumen 152 of the outer sheath 146.

Figure 13:
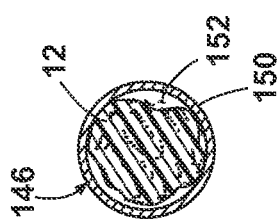
Figure 12:
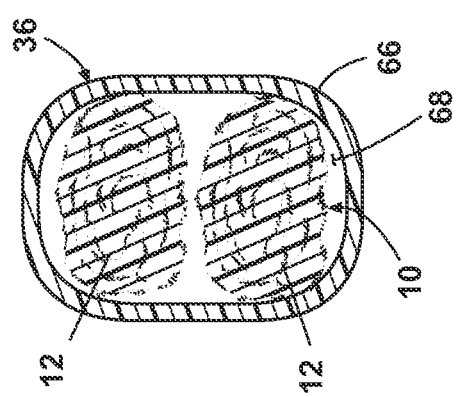

As the tether 14 pulls the implant 10 further distally into the outer sheath 146, the body 12 of the implant 10 converts from its expanded condition, an example of which is shown in FIG. 12, to the first compressed condition, shown in FIG. 13, as a result of the relatively small cross-sectional diameter of the side port 190 and the lumen 152; further, the taper of the side port 190 effectively forces the implant body 12 to compress in order to pass therethrough. Lengthening of the implant body 12 can accompany the compression.

Figure 14:
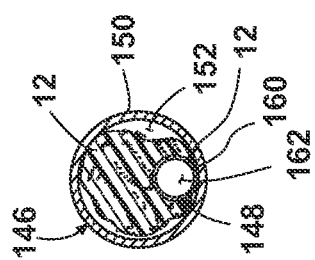
Figure 21:
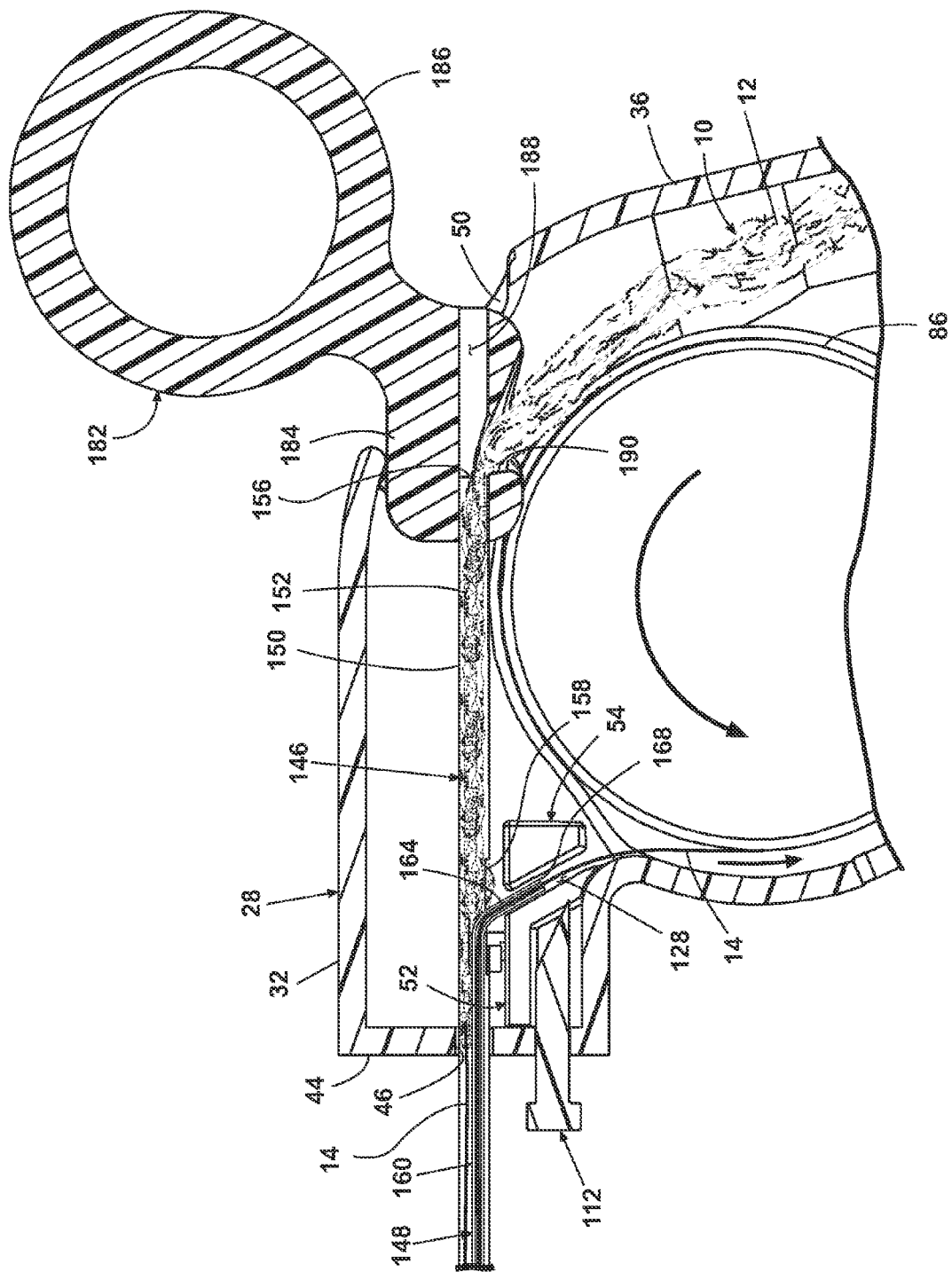

Referring to FIG. 21, as the tether 14 pulls the implant 10 further into the outer sheath 146, the implant 10 converts from the first compressed condition, shown in FIG. 13, to the second compressed condition, shown in FIG. 14, as a result of the entry of the inner sheath 148 into the lumen 152 of the outer sheath 146 at the aperture 158, which reduces the cross-sectional diameter of lumen 152 available for the implant 10 to pass through. The curvature of the inner sheath 148 at the proximal end region 164 facilitates the compression of the implant body 12 as it approaches the inner sheath 148 by gradually reducing the size of the space between the outer sheath 146 and the inner sheath 148. Further, a portion of the implant body 12 may temporarily expand to project out of the aperture 158 of the outer sheath 146 as that portion of the implant body 12 passes by the aperture 158, but is also gradually compressed as it encounters the proximal end region 164 of the inner sheath. The length of the implant body 12 can be selected so that the proximal end of the (compressed) implant body 12 is located just distal of the side port 190 or the hub 184 when the distal end of the implant body 12 has been advanced to the distal end of the inner sheath 148. As a result, there will be no excess implant material to interfere with the retraction and removal of the outer sheath 146.

The tether 14 and the implant 10 cease advancement when reaching the desired implant location, which is just below the sapheno-femoral junction H in the present example. The control lever 100 can be actuated a sufficient number of cycles, wherein each depression and release of the control lever 100 defines one cycle, to draw the implant to the desired implant location. FIG. 19 illustrates the implant 10 fully advanced into the greater saphenous vein B to just below the saphenofemoral junction H. In one embodiment, the practitioner advances the implant 10 until the distal end 16 of the implant body 12 is near or adjacent to the open distal end 154 of the shaft 150 of the outer sheath 146 as observed under imaging guidance, such as ultrasound guidance. Depending on the resolution of the imaging equipment and other factors, the distal end 16 of the implant body 12 can be flush with the open distal end 154 of the shaft 150 (i.e., the implant body 12 end does not project beyond the shaft 150), or the distal end 16 of the implant body 12 can project beyond the open distal end 154 of the shaft 150 when observed as being aligned. In another embodiment, the practitioner can advance the distal end 16 of the implant body 12 beyond the open distal end 154 of the shaft 150. In one embodiment, with the implant 10 fully advanced, the implant body 12 extends along the entire length of the lumen 152 of the shaft 150.

While the method of use of the system 20 is described in terms of advancement of the sheath assembly 26 and the implant 10 to place the implant 10 at the desired implant location, some proximal retraction of the sheath assembly 26 may also accompany the placement of the implant 10. Since the outer sheath 146 covers the inner sheath 148 and implant 10, the sheath assembly 26 can be retracted proximally to withdraw the inner sheath 148 and the implant 10, which is a useful feature in case the inner sheath 148 and the implant 10 are advanced beyond the desired implant location.

Figure 22:
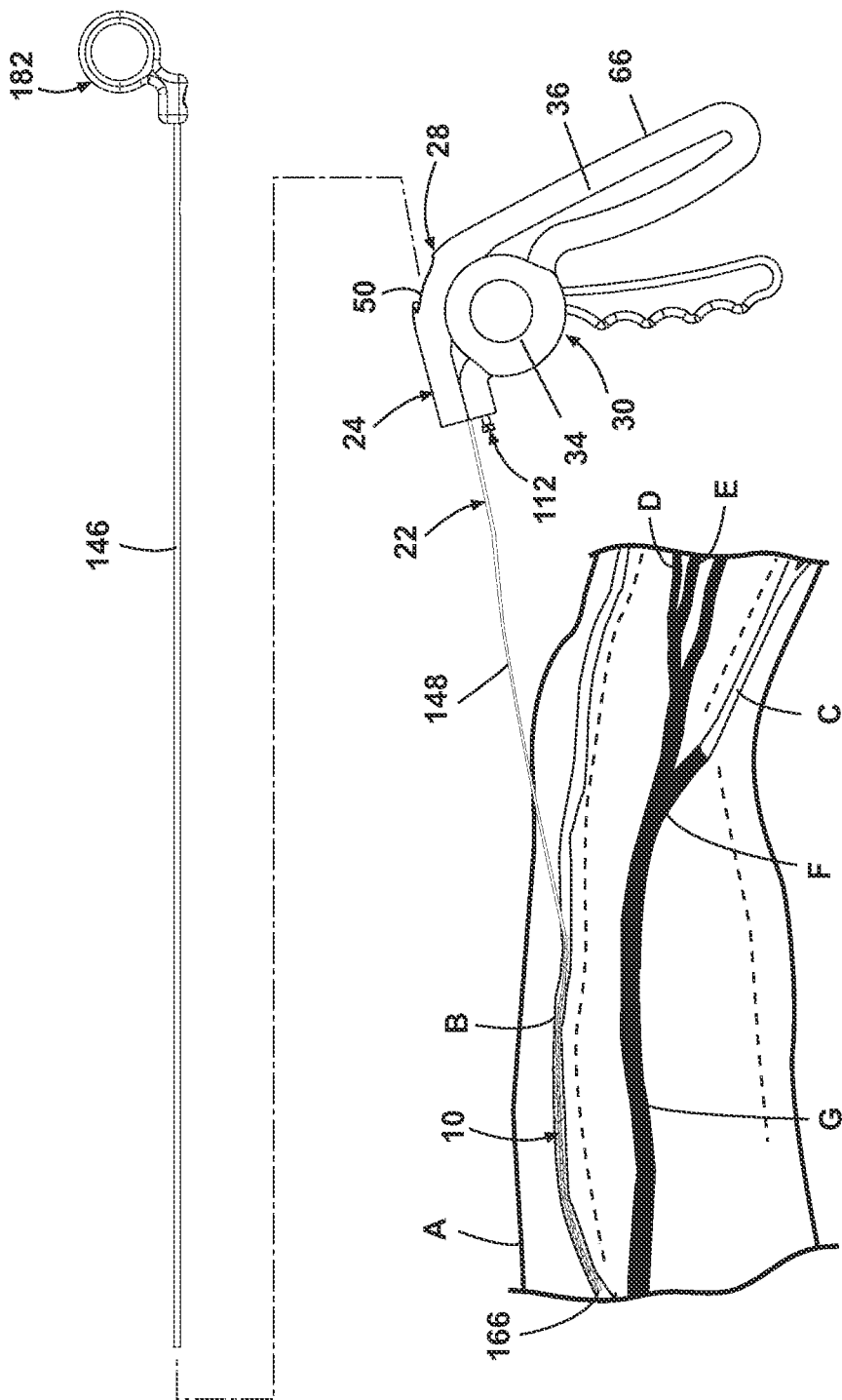

After the implant 10 is advanced to the desired implant location, the practitioner disconnects the outer sheath 146 from the housing 28 by gripping the handle 182 and pulling the outer sheath 146 proximally through the third aperture 50 and out of the housing 28, as illustrated in FIG. 22. This step may be preceded by the optional removal of a safety feature (not shown) preventing unwanted or inadvertent withdrawal of the outer sheath 146 from the housing 28.

Figure 23:
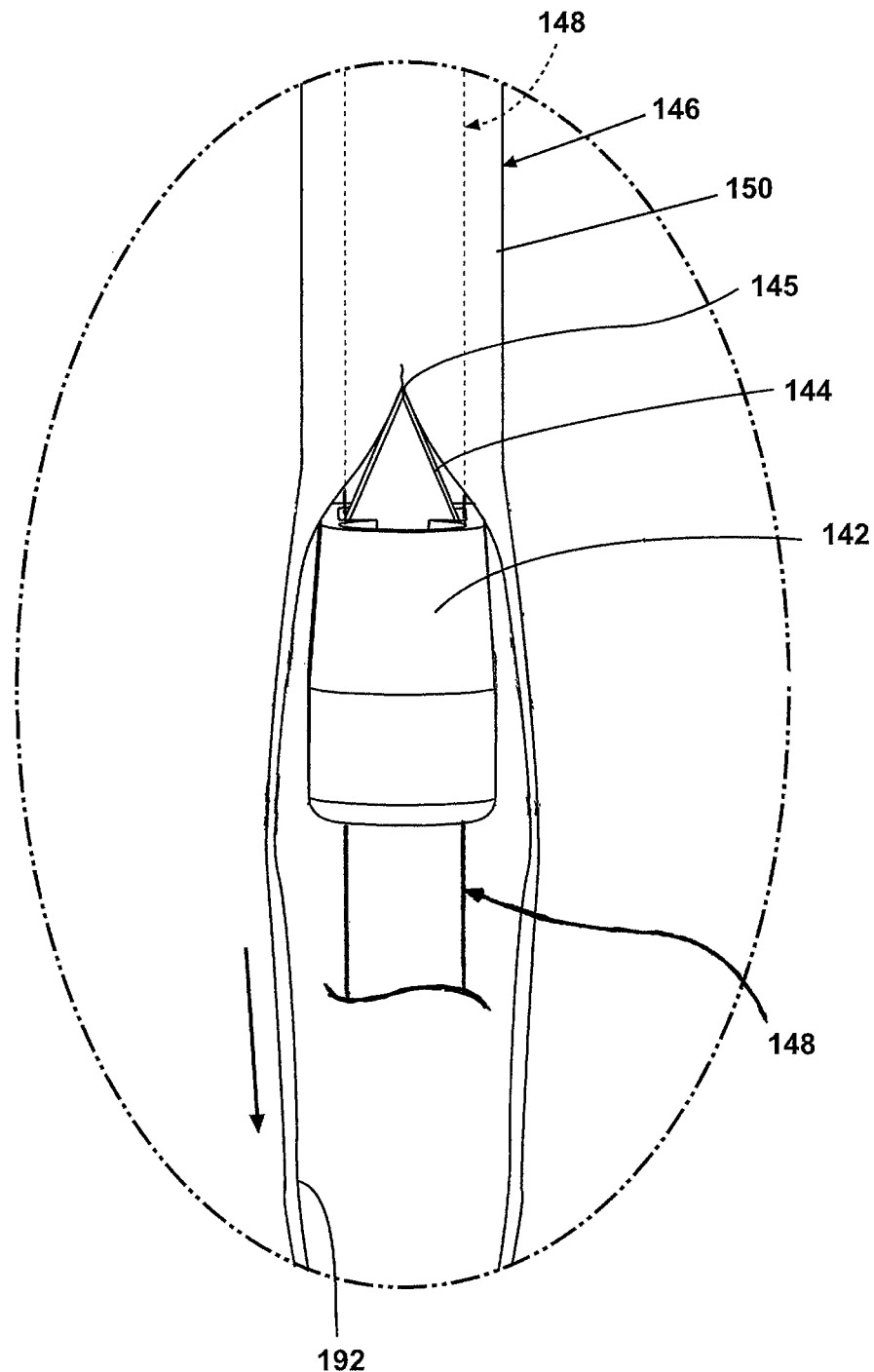

Referring to FIG. 23, which is a schematic underside view of the sheath cutting assembly 114, as the outer sheath 146 is pulled proximally, the blade 144 of the sheath cutting assembly 114 creates a cut 192 in the sidewall of the shaft 150 and the blade holder 142 parts the sidewall of the shaft 150 around the inner sheath 148, such that the outer sheath 146 can be removed without disturbing the position of the inner sheath 148. Furthermore, the inner sheath 148 is fixed to the blade holder 142 in the opening 143 thereof, thereby maintaining the position of the inner sheath 148 with respect to the housing 28 as the outer sheath 146 is withdrawn from the housing 28. In other words, the blade holder 142 securely holds, and prevents any substantial proximal movement of, the inner sheath 148 as the shaft 150 of the outer sheath 146 is retracted proximally over the inner sheath 148 (and implant 10, where present). As discussed above, in an alternate embodiment, the shaft 150 of the outer sheath 146 can be precut; in this case, the blade 144 of the sheath cutting assembly 114 may be a simple post or unsharpened wedge whose function is to simply initiate the parting of the precut shaft 150 to clear the inner sheath 148 as the outer sheath 146 is withdrawn from the housing 28 rather than create a new cut in the shaft 150.

Figure 24:
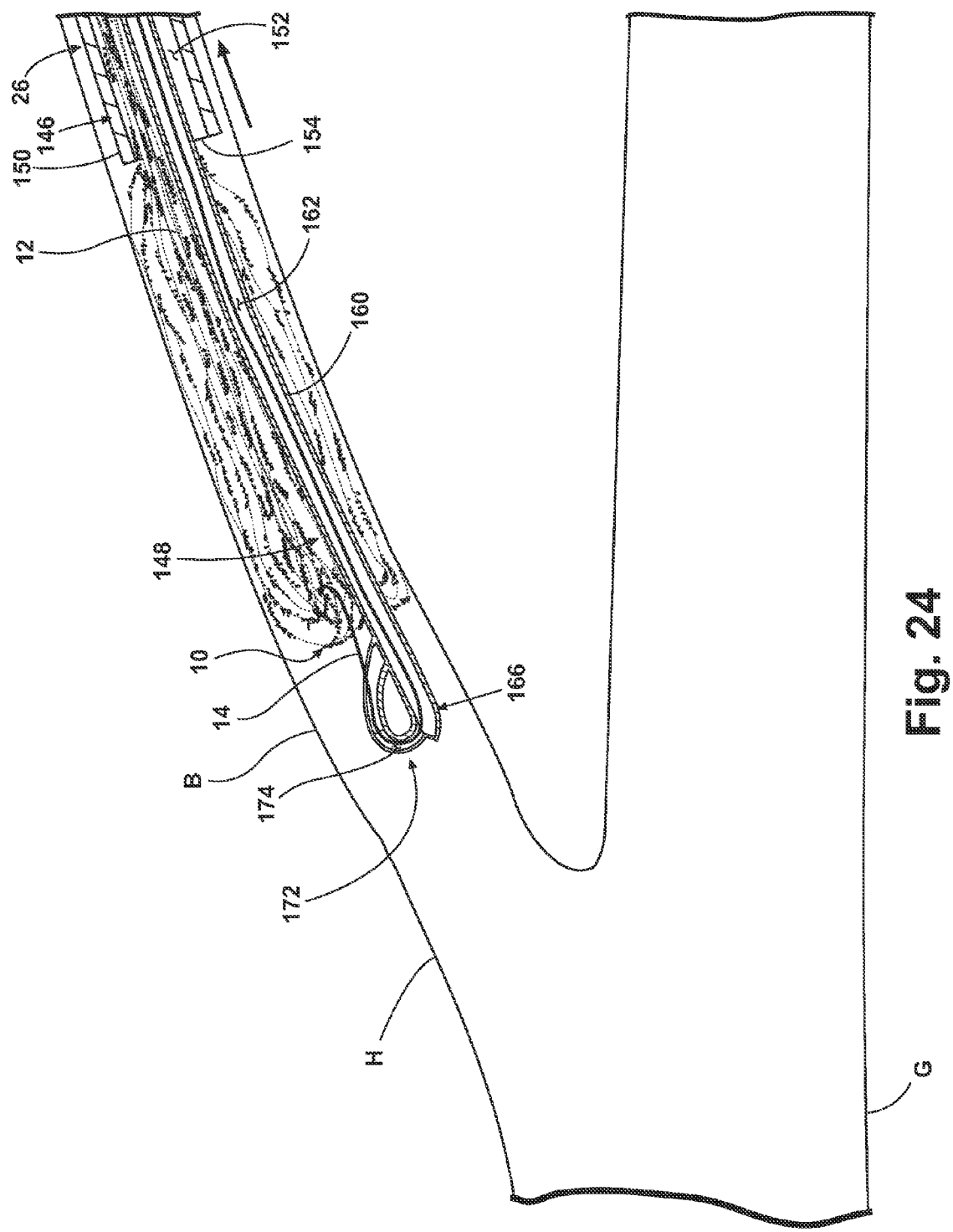
Figure 25:
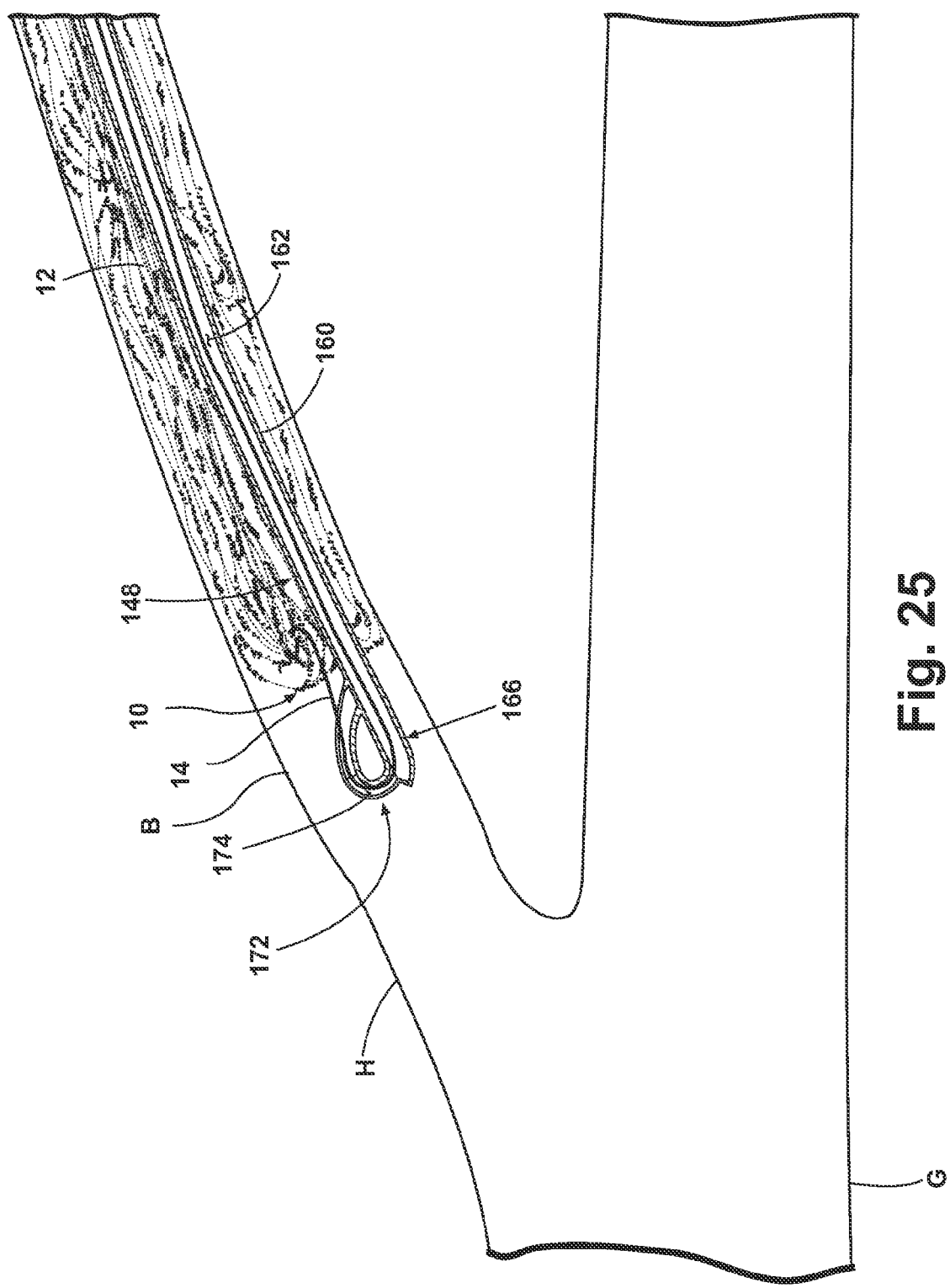

During the retraction and decoupling of the outer sheath 146, the inner sheath 148 and the implant 10 remain in the position shown in FIG. 24 in the vein B; thus, the outer sheath 146 moves proximally along and over the inner sheath 148, thereby exposing the inner sheath 148 and implant body 12. As the outer sheath 146 is retracted, it is withdrawn from the vein B, and the implant body 12 expands from the compressed condition when in the shaft 150 to effectively fill the vein B less the space occupied by the inner sheath 148. FIG. 25 illustrates the inner sheath 148 and the implant 10 in the greater saphenous vein B after complete removal of the outer sheath 146 from the vein B.

At this point, some proximal retraction of the inner sheath 148 can also accompany the placement of the implant 10. Since the inner sheath 148 and implant 10 are coupled by the tether 14, the inner sheath 148 can be retracted proximally to withdraw the distal portion of the implant 10 somewhat within the HAS, which is a useful step that can add additional bulk to distal portion of the implant 10 after it has been placed at the desired implant location.

Also after the implant 10 has been advanced to the desired implant location, the practitioner cuts the tether 14 using the tether cutting assembly 112. This step may be preceded by the optional removal of a safety feature (not shown) preventing unwanted or inadvertent actuation of the tether cutting assembly 112. In the illustrated embodiment, the tether 14 is cut after the outer sheath 146 has been removed.

Figure 26:
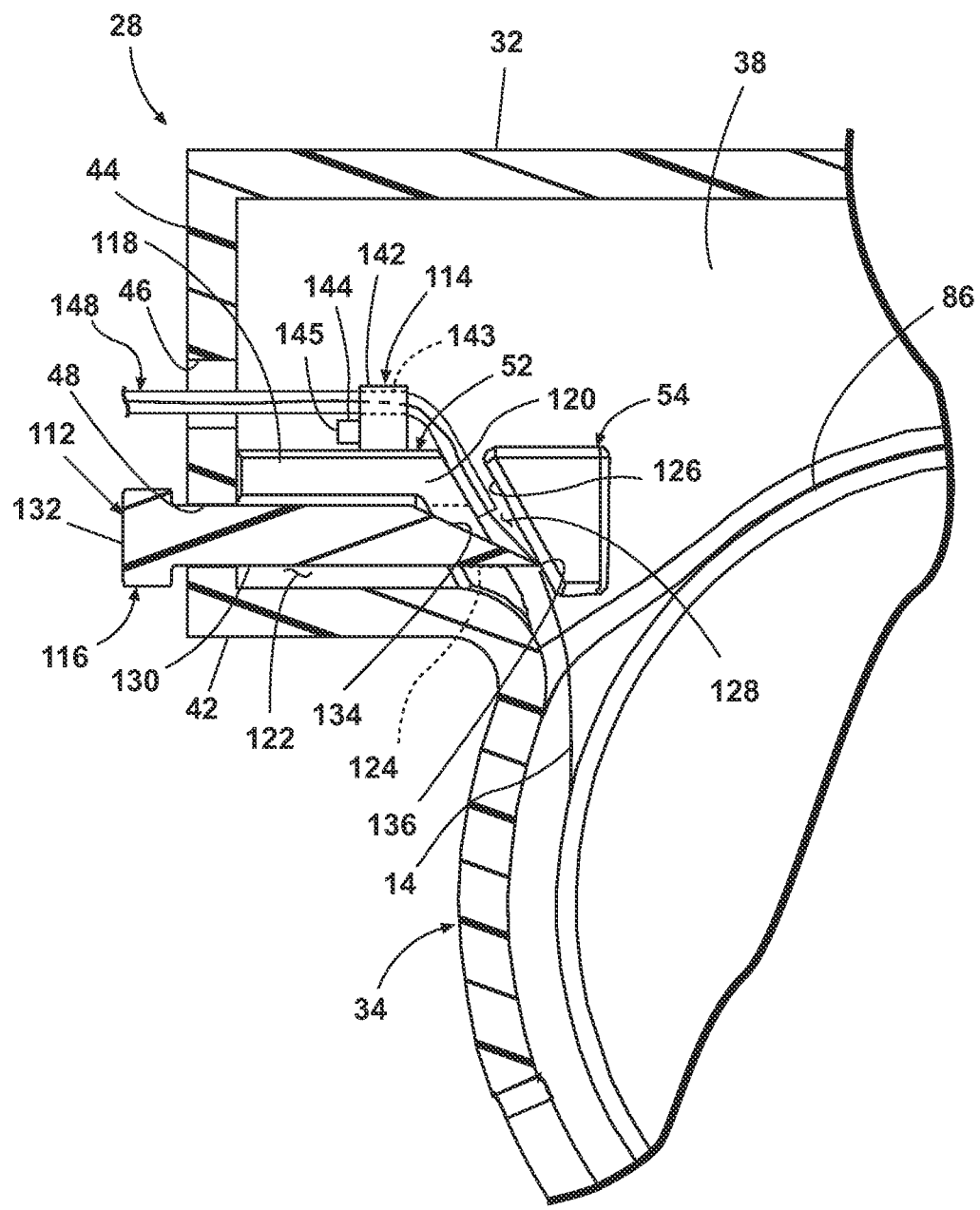

Referring to FIG. 26, to cut the tether 14, the practitioner applies proximal force to the trigger button 132 to move the cutting actuator 116 proximally within the guide channel 122. Continued application of proximal force causes the cutting element 134 project through the aperture 124 to engage the tether 14 in the channel 128 between the cutting guide 52 and the cutting block 54 and force the tether 14 against the cutting block 54. Specifically, the cutting edge 136 of the cutting element 134 presses the tether 14 against the cutting surface 126 of the cutting block 54, thereby severing the tether 14. Thereafter, a portion of the tether 14 remains coupled to the implant body 12, while the other portion of the tether 14 remains wound on the spool 86.

Figure 15:
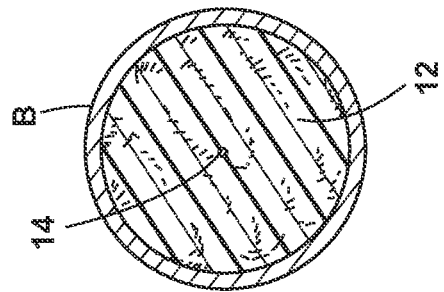
FIGS. 12-15 provide sectional views of a body of the implant of FIG. 2 in storage, first introduction, second introduction, and implantation conditions, respectively.
Figure 27:
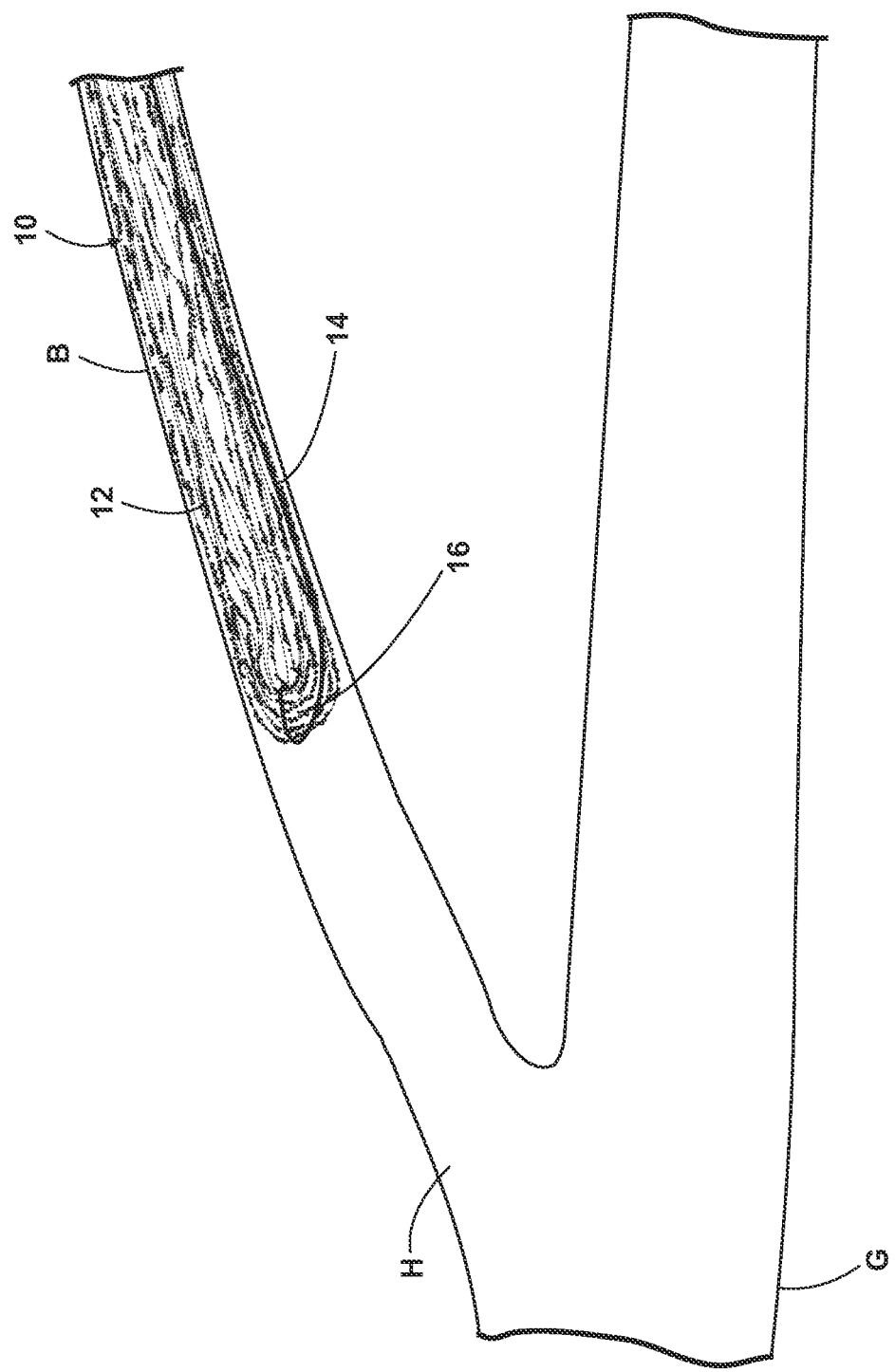

After cutting the tether 14 of the implant 10, the practitioner pulls apparatus 22 and, thus, the inner sheath 148, proximally away from the leg A to completely withdraw the inner sheath 148 from the vein B. Since the tether 14 has been cut, the tether 14 easily slides out of the inner sheath 148 as the inner sheath 148 is withdrawn. If desired, the practitioner can apply external compression to the vein B and the implant 10 to maintain the position of the implant 10 in the vein B. The distal end 16 of the implant 10 retains its position in the vein B during retraction of the inner sheath 148 due to its apposition against the vein wall, which can be aided with coagulation or "sticking" by any blood that is present in the vicinity. As the inner sheath 148 is withdrawn from the vein B, the implant body 12 expands to effectively fill the vein B. FIG. 27 illustrates the implant 10 in the greater saphenous vein B after removal of the inner sheath 148. FIG. 15 illustrates a cross-section of the greater saphenous vein B after implantation of the implant 10.

Upon removal of the inner sheath 148 and the storage/introducer unit 24, the implant 10 is situated in the vein B as shown in FIGS. 27 and 28, with the implant body 12 and tether 14 extending along the vein lumen from the distal tip of the implant 10 (in this case, near the junction H) toward the access site in the vein B. The tether 14 (and, if desired the implant body 12 as well) extend through the vein wall at the access site, and into the tissue tract formed during vein access and located in the subcutaneous tissue between the vein wall and the skin surface. The tether 14 (and, if desired, the implant body 12) pass through the tissue tract and emerge from the leg A at the skin surface. FIG. 29 shows the tether 14 emerging from the skin surface in this manner.

The practitioner can optionally secure the implant 10 to the leg A following removal of the inner sheath. In one embodiment, the tether 14 can be trimmed a desired length beyond the location where the tether 14 exits the leg A to bun a tether securing portion 194 projecting from the leg A. If the implant body 12 protrudes from the leg, the implant body 12 can also be trimmed at the location where the implant body 12 exits the leg A (i.e., the access site); however, because the apparatus 22 can employ a shorter implant 10 as discussed above, the implant body 12 may not protrude from the leg A once it is implanted, and trimming the implant body 12 may be unnecessary. The securing portion 194 can be taped or otherwise attached to the exterior surface, i.e., the skin, of the leg A, as shown in FIG. 28 and in greater detail in FIG. 29, which is an enlarged view of the exterior surface of the leg A, particularly the region of the leg A labeled "XXIX" in FIG. 28. With the distal end of the tether 14 attached to the distal end 16 of the implant body 12, and with the securing portion 194 attached to the skin, the tether 14 prevents migration of the implant 10 in the direction of the sapheno-femoral junction. In another embodiment, the implant 10, including the tether 14, can be secured to the access site by incorporation with access site sutures, such as 4-0 Vicryl braided or similar sutures. Where the implant body 12 extends into or through the access tissue tract as discussed above, the proximal end portion of the body 12 can be tucked into the tract within the subcutaneous tissue to enhance anchoring of the implant 10, or it can be secured to the skin surface as shown with the tether 14 in FIG. 29.

The order of the steps described above for the method of use of the system 20 can be performed in any desired and suitable order and are not intended to be limited to the order the steps are described above.

The method can be used with the illustrated apparatus 22, other embodiments of the illustrated apparatus 22, or other types of apparatus for storage and/or introduction of the implant 10 or other suitable implant. Similarly, the apparatus 22 can be employed with the illustrated implant 10, other embodiments of the illustrated implant 10, or other types of occluding implants. The case is the same with respect to the use of the sheath assembly 26 with the apparatus 22 and with respect to the use of the inner sheath 148 with the sheath assembly 26.

The apparatus 22 herein disclosed can be easily handled and manipulated by the practitioner using a single hand due to various aspects of the apparatus 22. One exemplary contributing aspect is the "gun-like" configuration of the storage/introducer unit 24, which permits the practitioner to hold the storage/introducer unit 24 and actuate the introducer assembly 30 to introducer the implant 10 into a HAS using a single hand. This leaves the practitioner's other hand free, which allows the practitioner to perform other actions during implant introduction, such as operating an imaging device, for example an ultrasonic device, to view the target HAS and the desired implant location.

The apparatus 22 can be provided as a ready-to-use kit having the implant 10 disposed in the implant storage portion 36 of the housing 28 and the tether 14 connected to the spool 86 and threaded through the sheath assembly 26 such that the apparatus 22 (e.g., as shown in FIGS. 3, 6, 9 and 11) can be removed from its packaging for immediate surgical use. In one embodiment, the apparatus 22 can be a single use device that is disposed after surgical use. Alternatively, the apparatus can be a multiple use device that can be sterilized and provided with a new implant 10 and, if necessary, a new outer sheath 146, for each surgical use.

The above description presents the best mode contemplated for carrying out the present apparatus and methods for storage and/or introduction of implant for hollow anatomical structure, and of the manner and process of practicing them, in such full, clear, concise, and exact terms as to enable any person skilled in the art to which they pertain to practice these apparatus and methods. These apparatus and methods are, however, susceptible to modifications and alternate constructions from those discussed above that are fully equivalent. Consequently, these apparatus and methods are not limited to the particular embodiments disclosed. On the contrary, these apparatus and methods cover all modifications and alternate constructions coming within the spirit and scope of these apparatus and methods as generally expressed by the following claims, which particularly point out and distinctly claim the subject matter of these apparatus and methods.

What is claimed is:

1. An apparatus for delivering an implant into a hollow anatomical structure, wherein the implant comprises an implant body and a tether having a first portion and a second portion, the first portion being coupled to a distal end of the implant body, the apparatus comprising:
   a housing defining an inner chamber and configured to contain the implant body within the inner chamber;
   an outer sheath having a proximal end attached to the housing and a distal end, the outer sheath defining a first lumen extending between the proximal and distal ends of the outer sheath;
   an inner sheath, at least a portion of which is contained within the first lumen and defining a space within the first lumen exterior to the portion of the inner sheath contained within the first lumen, the inner sheath having a distal end in the first lumen and defining a second lumen extending between the distal end of the inner sheath and a proximal end of the inner sheath,
   wherein the first lumen is configured to receive the first portion of the tether extending through the space, instead of the second lumen, in a distal direction, wherein the space is in communication with the inner chamber of the housing, and wherein the inner sheath is configured to receive the second portion of the tether extending in a proximal direction through the second lumen;
   a bearing surface in the first lumen adjacent the distal end of the outer sheath and the distal end of the inner sheath, the bearing surface configured to engage the tether between the first and second portions of the tether so as to cause the second portion of the tether to enter the distal end of the inner sheath and to extend in the proximal direction through the second lumen; and
   a tether movement mechanism operatively associated with the housing and configured to couple to the second portion of the tether, the tether movement mechanism being operable to move the second portion of the tether proximally within the second lumen and towards the tether movement mechanism, thereby to draw the implant body distally from the inner chamber of the housing and through the space of the first lumen; and further comprising an arched wall extending radially from the distal end of the inner sheath, an outer surface of the arched wall defining at least a portion of the bearing surface.

2. The apparatus of claim 1, wherein the tether movement mechanism comprises a reel configured to be coupled to the tether and operable to move the second portion of the tether proximally, and thereby draw the implant body distally along and within the first lumen.

3. The apparatus of claim 1, wherein the outer sheath is retractable proximally to expose the inner sheath and the implant once the implant is drawn distally from the inner chamber of the housing and through the space of the first lumen.

4. The apparatus of claim 3, further comprising a sheath parting member that projects into the first lumen through an opening in a sidewall of the outer sheath, wherein the sheath parting member is configured to part the sidewall of the outer sheath as the outer sheath is retracted proximally.

5. The apparatus of claim 4, wherein the sheath parting member is configured to cut through the sidewall of the outer sheath as the outer sheath is retracted.

6. The apparatus of claim 4, wherein the sidewall of the outer sheath has a score line and the sheath parting member is configured to split the sheath sidewall along the score line as the outer sheath is retracted.

7. The apparatus of claim 4, wherein:
the inner sheath includes a proximal portion of the inner member that comprises a lateral projection that turns and extends radially outward to pass out of the first lumen, at a location proximal of the sheath parting member,
such that the lateral projection of the inner sheath is positioned between two parted portions of the sidewall of the outer sheath as the outer sheath is retracted proximally and the sidewall of the outer sheath is parted.

8. The apparatus of claim 7, wherein the tether passes through the lateral projection of the inner sheath such that the inner sheath prevents contact between the sidewall of the outer sheath and the tether as the outer sheath is retracted proximally and the sidewall of the outer sheath is parted.

9. The apparatus of claim 1, wherein the inner sheath facilitates compression of the implant body from an expanded condition within the inner chamber of the housing to a compressed condition as the implant body is drawn distally through the space of the first lumen.

10. The apparatus of claim 9, wherein the outer sheath defines an aperture through which the inner sheath enters the outer sheath at an angle with respect to the outer sheath, and wherein a curvature of the inner sheath extending from the aperture reduces a size of the space within the first lumen to facilitate compression of the implant body as the implant body enters the space within the first lumen and exterior to the portion of the inner sheath.

11. The apparatus of claim 10, wherein the proximal end of the inner sheath extends out of the outer sheath through the aperture, the proximal end of the inner sheath defining a proximal opening configured for passage of the second portion of the tether toward the tether movement mechanism.

12. The apparatus of claim 1, wherein the arched wall comprises a semi-circular shape configured to retain the tether within the arched wall when tension is applied to the tether.

13. The apparatus of claim 1, wherein the inner sheath defines a distal opening, and wherein the outer surface of the arched wall is generally continuous with the distal opening.

14. The apparatus of claim 1, wherein the inner sheath and the arched wall are configured to be disposed within the first lumen.

15. A system for delivering an implant into a hollow anatomical structure, the system comprising:
the implant, the implant comprising an implant body and a tether having a first portion and a second portion, the first portion being coupled to a distal end of the implant body; and
an apparatus comprising:
a housing configured to contain the implant body;
an outer sheath having a proximal end attached to the housing and a distal end, the outer sheath defining a first lumen extending between the proximal and distal ends of the outer sheath;
an inner sheath, at least a portion of which is contained within the first lumen and defining a space within the first lumen exterior to the portion of the inner sheath contained within the first lumen, the inner sheath having a distal end in the first lumen and defining a second lumen extending between the distal end of the inner sheath and a proximal end of the inner sheath,
wherein the first lumen receives the first portion of the tether extending through the space in a distal direction, and wherein the inner sheath receives the second portion of the tether extending in a proximal direction through the second lumen;
a bearing surface in the first lumen adjacent the distal end of the outer sheath and the distal end of the inner sheath, the bearing surface configured to engage the tether between the first and second portions of the tether so as to cause the second portion of the tether to enter the distal end of the inner sheath and to extend in the proximal direction through the second lumen; and
a tether movement mechanism operatively associated with the housing and coupled to the second portion of the tether, the tether movement mechanism being operable to move the second portion of the tether proximally within the second lumen, thereby to draw the implant body distally through the outer sheath such that at least a portion of the implant body is disposed within the space within the first lumen and exterior to the portion of the inner sheath contained within the first lumen.

* * * * *